US009764044B2

(12) United States Patent
Verfaillie et al.

(10) Patent No.: US 9,764,044 B2
(45) Date of Patent: Sep. 19, 2017

(54) HOMOLOGOUS RECOMBINATION IN MULTIPOTENT ADULT PROGENITOR CELLS

(75) Inventors: Catherine Verfaillie, Leuven (BE); Uma Lakshmipathy, Carlsbad, CA (US)

(73) Assignee: ABT HOLDING COMPANY, Cleveland, OH (US)

( * ) Notice: Subject to any disclaimer, the term of this patent is extended or adjusted under 35 U.S.C. 154(b) by 0 days.

(21) Appl. No.: 12/784,579

(22) Filed: May 21, 2010

(65) Prior Publication Data
US 2010/0285590 A1 Nov. 11, 2010

Related U.S. Application Data

(62) Division of application No. 10/536,716, filed as application No. PCT/US03/38811 on Nov. 25, 2003, now abandoned.

(51) Int. Cl.
  *C12N 15/85* (2006.01)
  *A61K 48/00* (2006.01)
  *C12N 15/10* (2006.01)

(52) U.S. Cl.
  CPC ........ *A61K 48/005* (2013.01); *C12N 15/1082* (2013.01)

(58) Field of Classification Search
  None
  See application file for complete search history.

(56) References Cited

U.S. PATENT DOCUMENTS

| | | | |
|---|---|---|---|
| 5,486,359 A | 1/1996 | Caplan et al. | |
| 5,827,735 A | 10/1998 | Young et al. | |
| 6,090,625 A | 7/2000 | Abuljadayel | |
| 6,514,752 B1 * | 2/2003 | Kucherlapati et al. | 435/320.1 |
| 6,653,134 B2 | 11/2003 | Prockop et al. | |
| 6,777,231 B1 | 8/2004 | Katz et al. | |
| 7,045,148 B2 | 5/2006 | Hariri | |
| 7,056,738 B2 | 6/2006 | Prockop et al. | |
| 7,229,827 B2 | 6/2007 | Kim et al. | |
| 7,311,905 B2 | 12/2007 | Hariri | |
| 2001/0033834 A1 | 10/2001 | Wilkison et al. | |
| 2001/0046489 A1 | 11/2001 | Habener et al. | |
| 2002/0061587 A1 | 5/2002 | Anversa | |
| 2002/0164794 A1 | 11/2002 | Wernet | |
| 2003/0003090 A1 | 1/2003 | Prockop et al. | |
| 2003/0032179 A1 | 2/2003 | Hariri | |
| 2003/0059414 A1 | 3/2003 | Ho et al. | |
| 2004/0235165 A1 | 11/2004 | Prockop et al. | |
| 2005/0169896 A1 | 8/2005 | Li et al. | |
| 2006/0177925 A1 | 8/2006 | Rosenberg et al. | |

FOREIGN PATENT DOCUMENTS

| | | |
|---|---|---|
| WO | WO 96/23870 | 8/1996 |
| WO | WO 99/16863 | 4/1999 |
| WO | WO 99/35243 | 7/1999 |
| WO | WO 01/04268 | 1/2001 |
| WO | WO 01/11011 * | 1/2001 |
| WO | WO 01/08691 | 2/2001 |
| WO | WO 01/21766 | 3/2001 |
| WO | WO 01/21767 | 3/2001 |
| WO | WO 01/62901 | 8/2001 |
| WO | WO 02/08388 | 3/2002 |
| WO | WO 02/34890 | 5/2002 |

OTHER PUBLICATIONS

Amax flyer online 2011.*
Cambrex specimens, "Poietics Human Mesenchymal Stem Cell Systems," Cambrex BioScience Walkersville, Inc. (2005).
Prockop, D., "Marrow stromal cells as stem cells for nonhematopoietic tissues" Science; 276:71-74 (1997).
Bjornson et al., "Turning brain into blood: a hematopoietic fate adopted by adult neural stem cells in vivo" Science; 283:534-537 (1999).
Reyes et al., "Purification and ex vivo expansion of postnatal human marrow mesodermal progenitor cells" Blood; 98:2615-25 (2001).
Bouwens, L., "Transdifferentiation versus stem cell hypothesis for the regeneration of islet beta-cells in the pancreas" Microscopy Research and Technique; 43:332-336 (1998).
Reyes et al., "Origin of endothelial progenitors in human postnatal bone marrow" J. Clin. Invest; 109:1-10 (2002).
Reyes et al., "Characterization of multilineage mesodermal progenitor cells in adult marrow" Abstract No. 124, American Society for Hematology (2001).
Reyes et al., "Turning marrow into brain; generation of glial and neuronal cells from adult bone marrow mesenchymal stem cells" Abstract No. 1676, American Society for Hematology (2001).
Reyes et al., "Skeletal smooth and cardiac muscle differentiation from single adult marrow derived mesodermal progenitor cells" Abstract No. 2610, American Society for Hematology (2001).
Reyes et al,, "In vitro and in vivo characterization of neural cells derived from mesenchymal stem cells" Abstract 2126, American Society for Hematology (2001).
Reyes et al., "Endothelial cells generated from human marrow derived mesenchymal stem cells (MSC)" Abstract No. 2276, American Society for Hematology (2001).
Zhao et al., "Immunohistochemical identification of multipotent adult progenitor cells from human bone marrow after transplantation into the rat brain" Brain Res Brain Res Protoc; 11;38-45 (2003).
Jiang et al., "Multipotent progenitor cells can be isolated from postnatal murine bone marrow, muscle, and brain" Exp. Hematol.; 30:896-904 (2002).

(Continued)

*Primary Examiner* — Celine Qian
(74) *Attorney, Agent, or Firm* — Tarolli, Sundheim, Covell & Tummino LLP

(57) ABSTRACT

The invention relates to methods of altering gene expression by homologous recombination in a multipotent adult progenitor cell (MAPC). In particular, methods of producing a recombinant MAPC, of correcting a genetic defect in a mammal, of providing a functional and/or therapeutic protein to a mammal, and of transforming a MAPC are provided. MAPCs containing an erogenous DNA as well as recombinant MAPCs and their differentiated progeny are also provided.

11 Claims, 9 Drawing Sheets

(56) References Cited

OTHER PUBLICATIONS

Jiang et al., "Pluripotency of mesenchymal stem cells derived from adult marrow" Nature; 418:41-49 (2002).
Schwartz, R., "Multipotent adult progenitor cells from bone marrow differentiate into hepatocyte-like cells" J Clin Invest.; 109:1291-1302 (2002).
Zhao et al., "Human bone marrow stem cells exhibit neural phenotypes and ameliorate neurological deficits after grafting into the ischemic brain of rats" Exp Neurol; 174:11-20 (2002).
Lamming et al., "Spontaneous circulation of myeloid-lymphoid-initiating cells and SCID-repopulating cells in sickle cell crisis" J. Clin. Invest.; 111:811-819 (2003).
Qi et al., "Identification of genes responsible for osteoblast differentiation from human mesodermal progenitor cells" Nat. Acad. Sci. USA; 100:3305-3310 (2003).
Verfaillie, C. "Investigator Profile" Journal of Hematotherapy and Stem Cell Research; 11:441-444 (2002).
Verfaillie et al., "Stem cells: hype and reality" Hematology (Am Soc Hematol Educ Program); 369-391 (2002).
Verfaille, C., "Optimizing hematopoietic stem cell engraftment: a novel role for thrombopoeitin" J. Clin. Invest.; 110:303-304 (2002).
Liu et al., "Myeloid-lymphoid-initiating cells (ML-IC) are highly enriched in the rhodamine-C-Kit(+) CD33(−)CD38(−) fraction of umbilical cord CD34(+)" Exp. Hematol.; 30:582-589 (2002).
Lewis et al., "Multi-lineage expansion potential of primitive hematopoietic progenitors: superiority of umbilical cord blood compared to mobilized peripheral blood" Exp. Hematol.; 28:1087-1095 (2002).
Verfaillie, C.M., "Meeting Report on an NHLBI Workshop on ex vivo expansion of stem cells, Jul. 29, 1999, Washington D.C. National Heart Lung and Blood Institute" Exp. Hematol.; 28:361-364 (2000).
Punzel et al., "The myeloid-lymphoid initiating cell (ML-IC) assay assesses the fate of multipotent human progenitors in vitro" Blood; 93:3750-3756 (1999).
Roy et al., "Expression and function of cell adhesion molecules on fetal liver, cord blood and bone marrow hematopoietic progenitors: implications for anatomical localization and developmental stage specific regulation of hematopoiesis" Exp. Hematol.; 27:302-312 (1999).
Miller et al., "Ex vivo culture of CD34+/Lin−/DR− cells in stroma-derived soluble factors, interleukin-3, and macrophage inflammatory protein-1 alpha maintains not only myeloid but also lymphoid progenitors in a novel switch culture assay" Blood; 15:4516-4522 (1998).
Verfaillie, C., "Stem cells in chronic myelogenous Leukemia" Hematol. Oncol. Clin. North Am.; 11:1079-1114 (1997).
Prosper et al., "Phenotypic and functional characterization of long-term culture-initiating cells present in peripheral blood progenitor collections of normal donors treated with granulocyte colony-stimulating factor" Blood; 15:2033-2042 (1996).
Lodie et al., "Systematic analysis of reportedly distinct populations of multipotent bone marrow-derived stem cells reveals a lack of distinction" Tissue Engineering; 8:739-751 (2002).
Pagen Westphal, S., "Adult bone marrow eyed as source of stem cells" Boston Globe, Jan. 24, 2002.
Pagen Westphal, S., "Ultimate stem cell discovered" New Scientist, Jan. 23, 2002.
Wade et al., "Scientists herald a versatile adult cell" The New York Times on the Web, Jan. 25, 2002.
Rosford et al., "The octamer motif present in the Rex-1 promoter binds Oct-1 and Oct-3 expressed by EC cells and ES cells" Biochem. Biophys. Res. Comm.; 203:1795-1802 (1994).
Rosner et al., "Oct-3 is a maternal factor required for the first mouse embryonic division" Cell; 64:1103-1110 (1991).
Pittenger et al., "Multilineage potential of adult human mesenchymal stem cells"; Science; 284:143-147 (1999).
Ben-Shushan et al., "Rex1, a gene encoding a transcription factor expressed in the early embryo, is regulated via Oct-3/4 and Oct-6 binding to and octamer site and a novel protein, R ox-1, binding to an adjacent site" Mol. Cell Biol.; 18:1866-1878 (1998).
Reyes et al., "Characterization of multipotent adult progenitor cells, a subpopulation of mesenchymal stem cells" Annals of the New York Academy of Science; 938:231-235 (2001).
Anjos-Afonso and Bonnet,"Nonhematopoietic/endothelial SSE-1+ cells define the most primitive progenitors in the adult murine bone marrow mesenchymal compartment" Blood; 109:1298-1306 (2007).
Bertani et al., "Neurogenic potential of human mesenchymal stem cells revisited: analysis by immunostaining, time-lapse video and microarray" J Cell Sci.; 118:3925-36 (2005).
Bodnar et al., "Extension of life-span by introduction of telomerase into normal human cells" Science; 279:349-352 (1998).
Horwitz et al., "Clarification of the nomenclature for MSC: the international society for cellular therapy position paper" Cytotherapy; 7:393-395 (2005).
Lu et al., "Induction of bone marrow stromal cells to neurons: differentiation, transdifferentiation, or artifact" J Neurosci Res; 77:174-91 (2004).
Neuhuber et al., "Reevaluation of in vitro differentiation protocols for bone marrow stromal cells: disruption of actin cytoskeleton induces rapid morphological changes and mimics neuronal phenotype"J Neurosci Res; 77:192-204 (2004).
Simonsen et al., "Telomerase expression extends the proliferative life-span and maintains the osteogenic potential of human bone marrow stromal cells" Nature Biotechnology; 20:592-596 (2002).
Zimmerman et al., "Lack of telomerase activity in human mesenchymal stem cells" Leukemia; 17:1146-1149 (2003).
Izadpanah et al., "Biologic properties of mesenchymal stem cells derived from bone marrow and adipose tissue" Journal of Cellular Biochemistry; 99:1285-1297 (2006).
Long et al., "Neural cell differentiation in vitro from adult human bone marrow mesenchymal stem cells" Stem Cells and Development; 14:65-69 (2005).
Moriscot et al., "Human bone marrow mesenchymal stem cell can express insulin and key transcription factors of the endocrine pancreas developmental pathway upon genetic and/or microenvironmental manipulation in vitro" Stem Cells; 23:594-604 (2005).
Sanchez-Ramos et al., "Adult bone m arrow stromal cells differentiate into neural cells in vitro" Exp. Neurol.; 164:247-56 (2000).
Eglitis et al., "Hematopoietic cells differentiate into both microglia and macroglia in the brain of adult mice" Proc. Natl. Acad. Sci. USA; 94:4080-85 (1997).
Kopen et al., "Marrow stromal cells migrate throughout forebrain and cerebellum, and they differentiate into astrocytes after injection into neonatal mouse brains" Proc. Natl. Acad. Sci. USA; 96:10711-16 (1999).
Lagasse et al., "Purified hematopoietic stem cells can differentiate into hepatocytes in vivo" Nature Medicine; 6:1229-1234 (2000).
Wang, X. et al., "Cell fusion is the principal source of bone-marrow-derived hepatocytes" Nature; 422:897-901 (2003).
Giles, J., "The trouble with replication" Nature, 422:344-347 (2006).
Verfaillie, C.M., Multipotent adult progenitor cells: an update: Novartis Found Symp., 254:55-65 (2005).
Aldhous et al., "Fresh questions on stem cell findings" New Scientist, Mar. 21, 2007.
Brazelton et al., "From marrow to brain: expression of neuronal phenotypes in adult mice" Science; 290:1775-9 (2000).
Clarke et al., "Generalized potential of adult neural stem cells" Science; 288: 1660-3 (2000).
Johansson et al., "Neural stem cells in the adult human brain" Exp. Cell. Res.; 253:733-6 (1999).
Mezey et al., "Turning blood into brain: cells bearing neuronal antigens generated in vivo from bone marrow" Science; 290:1779-82 (2000).
Morshead et al., "Hematopoietic competence is a rare property of neural stem cells that may depend on genetic and epigenetic alterations" Nat. Med.; 8:268-73 (2002).
Petersen et al., "Bone marrow as a potential source of hepatic oval cells" Science; 284:1168-70 (1999).

(56) References Cited

OTHER PUBLICATIONS

Scintu et al., "Differentiation of human bone marrow stem cells into cells with a neural phenotype: diverse effects of two specific treatments" BMC Neurosci.; 7:14 (2006).

U.S. Patent and Trademark Office, Office Action dated Jun. 24, 2005 in related U.S. Appl. No. 10/040,757.

U.S. Patent and Trademark Office, Office Action and 892 dated Jun. 27, 2008 in related U.S. Appl. No. 10/467,963.

U.S. Patent and Trademark Office, Office Action dated Oct. 15, 2009 in related U.S. Appl. No. 10/467,963.

U.S. Patent and Trademark Office, Office Action and 892 dated Apr. 7, 2008 in related U.S. Appl. No. 11/151,689.

U.S. Patent and Trademark Office, Office Action dated Jan. 4, 2006 in related U.S. Appl. No. 11/238,234.

U.S. Patent and Trademark Office, Office Action dated Aug. 29, 2006 in related U.S. Appl. No. 11/238,234.

U.S. Patent and Trademark Office, Office Action and 892 dated Apr. 3, 2007 in related U.S. Appl. No. 11/238,234.

U.S. Patent and Trademark Office, Office Action dated Oct. 7, 2008 in related U.S. Appl. No. 11/238,234.

Communication and 1449, filed Oct. 2, 2007 in related U.S. Appl. No. 11/238,234, and supplemental 1449 submitted on Oct. 4, 2007.

Information Disclosure Statement, Second Communication and PTO/SB/08b, filed Dec. 24, 2008 in related U.S. Appl. No. 11/238,234.

Hatada et al., "Gene correction in hematopoietic progenitor cells by homologous recombination" PNAS 97:13807-13811 (2000).

Lamming et al., "Efficient Transfection of Human CD34+ Cells with 'Sleeping Beauty'" Blood 100:654a-655a, Abstract 2574 (2002).

Jahagirdar et al., "Engraftment and Tissue Specific Differentiation of Multipotent Adult Progenitor Cells from Human Marrow in Epithelium, the Hematopoietic System and Endothelium In vivo" Blood 98:547a, Abstract 2289 (2001).

Hsieh et al., "Histone Deacetylase inhibition-mediated neuronal differentiation of multipotent adult neural progenitor cells" PNAS 101:16659-16664 (2004).

Masson et al., "Potential of Hematopoietic Stem CVell Therapy in Hepatology: A Critical Review" Stem Cells 22:897-907 (2004).

\* cited by examiner

Figure 8

```
ATGGCTCAAGATTCAGTAGATCTTTCTTGTGATTATCAGTTTTGGATGCA    50
GAAGCTTTCTGTATGGGATCAGGCTTCCACTTTGGAAACCCAGCAAGACA   100
CCTGTCTTCACGTGGCTCAGTTCCAGGAGTTCCTAAGGAAGATGTATGAA   150>
GCCTTGAAAGAGATGGATTCTAATACAGTCATTGAAACTTGAAAGATTCCCCACAT   200>
TGGTCAACTGTTGGCAAAAGCTTGTTGGAATCCTTTATTTTAGCATATG    250>
ATGAAAGCCAAAAAATTCTAATATGGTGCTTATGTTGTCTAATTAACAAA   300>
GAACCACAGAATTCTGGACAATCAAAACTTAACTCCTGGATACAGGGTGT   350>
ATTATCTCATATACTTTCAGCACTCAGATTTGATAAAGAAGTTGCTCTTT   400>
TCACTCAAGGTCTTGGGTATGCACCTATAGATTACTATCCTGGTTTGCTT   450>
AAAAATATGGTTTTATCATTAGCGTCTGAACTCAGAGAGAATCATCTTAA   500>
TGGATTTAACACTCAAAGGCGAATGGCTCCCGAGCGAGTGGCGTCCCTGT   550>
CACGAGTTTGTGTCCCACTTATTACCCTGACAGATGTTGACCCCCTGGTG   600>
GAGGCTCTCCTCCTCATCTGTCATGGACGTGAACCTCAGGAAATCCTCAGCC   650>
AGAGTTCTTTGAGGCTGTAAACGAGGCCATTTTGCTGAAGAAGATTTCTC   700>
TCCCATGTCAGCTGTAGTCTGCCTCTGGCTTCGGCACCTTCCCAGCCTT   750>
GAAAAAGCAATGCTGCATCTTTTTGAAAAGCTAATCTCCAGTGAGAGAAA   800>
TTGTCTGAGAAGGATCGAATGCTTTATAAAGATTCATCGCTGCCTCAAG   850>
CAGCCTGCCACCTGCCATATTCCGGGTTGTTGATGAGATGTTCAGGTGT   900>
GCACTCCTGGAAACCGATGGGCCCTGAAATCATAGCCACTATTCAGGT   1000>
GTTTACGCAGTGCTTTGTAGAAGCTCTGGAGAAAGCAAGCAGCTGC      1050>
GGTTTGCACTCAAGACCTACTTTCCTTACACTTCTCCATCTCTTGCCATG  1100>
GTGCTGCTGCAAGACCCTCAAGATATCCTCGGGGACACTGGCTCCAGAC   1150>
ACTGAAGCATATTTCTGAACTGCTCAGAGAAGCAGTTGAAGACCAGACTC  1200>
ATGGGTCCTGCGGAGGTCCCTTTGAGAGCTGGTTCCTGTTCATTCACTTC  1250>
GGAGGATGGGCTGAGATGGGTGGCAGAGCAATTACTGATGTCGGCAGCCGA 1300>
ACCCCCACGGCCCTGCTCTGTGCTCTTGGCCTTCTCAGGTGAAGGCTGT   1350>
ATGGGAGGCAGAGAGCACAGACTATGGTCCAGGTGAAGGCCGTGCTGGGC  1400>
CACCTCCTGGCAATGTCCAGAGGCACAGCAGCAGCTCTCAGCCTCTGCA   1450>
GACGGTAGCAGGACACCTTCCTCCCAACTTCCTGCTCTGGCTCCTGAGGC  1500>
AGCTGATCAGGCACCTTCTCATCACCCTGATGCTCACACTGCTGAGAT    1550>
CACAGATCGCCTGGGATGTCATCAACCGAGACCTTGTACAGATGGAATC   1600>
AACTCACGAGATCATTGGCTTTCTTGACCAGACCTTGTACAGATGAATC   1650>
GTCTTGGCATTGAAAGCCCTAGATCAGAAAAACTGGCCCGAGAGCTCCTT  1700>
AAAGAGCTGCGAACTCAAGTCTAG 1724
```

Figure 9

```
MAQDSVDLSCDYQFWMQKLSVWDQASTLETQQDTCLHVAQFQEFLRKMYE    50
ALKEMDSNTVIERFPTIGQLLAKACWNPFILAYDESQKILIWCLCCLINK   100
EPQNSGQSKLNSWIQGVLSHILSALRFDKEVALFTQGLGYAPIDYYPGLL   150
KNMVLSLASELRENHLNGFNTQRRMAPERVASLSRVCVPLITLTDVDPLV   200
EALLICHGREPQEILQPEFFEAVNEAILLKKISLPMSAVVCLWLRHLPSL   250
EKAMLHLFEKLISSERNCLRRIECFIKDSSLPQAACHPAIFRVVDEMFRC   300
ALLETDGALEIIATIQVFTQCFVEALEKASKQLRFALKTYFPYTSPSLAM   350
VLLQDPQDIPRGHWLQTLKHISELLREAVEDQTHGSCGGPFESWFLFIHF   400
GGWAEMVAEQLLMSAAEPPTALLWLLAFYYGPRDGRQRAQTMVQVKAVLG   450
HLLAMSRSSSLSAQDLQTVAGQGTDTDLRAPAQQLIRHLLLNFLLWAPGG   500
HTIAWDVITLMAHTAEITHEIIGFLDQTLYRWNRLGIESPRSEKLARELL   550
KELRTQV.   558
```

HOMOLOGOUS RECOMBINATION IN MULTIPOTENT ADULT PROGENITOR CELLS

RELATED APPLICATIONS

This application claims the benefit of priority to U.S. application Ser. No. 60/429,631, filed on Nov. 27, 2002. This application makes reference to International Application No. PCT/US00/21387, filed Aug. 4, 2000 and to International Application No. PCT/US02/04652, filed Feb. 14, 2002, both of which are hereby incorporated by reference. Each document cited or referenced in each of the foregoing applications, and any manufacturer's instructions or catalogues for any products cited or mentioned in each of the foregoing applications and in any of the cited documents, are hereby incorporated herein by reference. Furthermore, all documents cited in this text, and all documents cited or referenced in documents cited in this text, and any manufacturer's instructions or catalogues for any products cited or mentioned in this text or in any document incorporated into this text, are incorporated herein by reference. Documents incorporated by reference into this text or any teachings therein can be used in the practice of this invention. Documents incorporated by reference into this text are not admitted to be prior art.

FIELD OF THE INVENTION

The present invention relates generally to alteration of gene expression in mammalian multipotent adult progenitor cells (MAPCs) [previously referred to as multipotent adult stem cells (MASC)], and more specifically to methods for making homologously recombined MAPCs. The invention further relates to the therapeutic treatment of disease using homologous recombination and gene targeting techniques in MAPCs.

BACKGROUND OF THE INVENTION

The alteration of gene expression, by upregulating, down-regulating, knocking-in or knocking-out gene products, can be accomplished using gene targeting approaches, such as homologous recombination. Gene targeting approaches are an alternative for both in vitro and in vivo production of proteins. In vitro expression of desired proteins has multiple uses, from production of therapeutic drugs to generating nutrients to providing drug and disease screening and research tools. An aspect of gene targeting involves gene therapy, which has been advanced as a treatment for medical conditions that require alteration of the level of protein production in a cell, whether ex vivo or in vivo, and, if necessary, the delivery of such protein(s) to other cells and tissues.

An aspect of gene targeting ex vivo involves transfection and transplantation of recombinant autologous or allogeneic cells. As one example, stem cells provide promise for improving the results of such cell-based gene targeting. Stem cells can be genetically altered in vitro, then reintroduced in vivo to produce a desired gene product.

The quintessential stem cell is the embryonic stem (ES) cell, as it has unlimited self-renewal and multipotent differentiation potential (Thomson et al., 1995; Thomson et al., 1998; Shamblott et al., 1998; Williams et al., 1988; Orkin, 1998; Reubinoff et al., 2000). These cells are derived from the inner cell mass of the blastocyst (Thomson et al., 1995; Thomson et al., 1998; Martin, 1981), or can be derived from the primordial germ cells from a post-implantation embryo (embryonal germ cells or EG cells). ES and EG cells have been derived from mouse, and more recently also from non-human primates and humans. When introduced into mouse blastocysts, ES cells have been shown to contribute to tissues from all three germ layers of the mouse (Orkin 1998). ES cells are therefore pluripotent.

Stem cells that are not isolated from an embryo are simply referred to as stem cells or sometimes tissue-specific stem cells or adult stem cells. Stem cells have been identified in most organs and tissues. A well-characterized stem cell is the hematopoietic stem cell ("HSC"). This mesoderm-derived cell has been purified based on cell surface markers and functional characteristics. The HSC, isolated from bone marrow ("BM"), blood, cord blood, fetal liver and yolk sac, is the progenitor cell that generates blood cells, or following translation, reinitiates multiple hematopoietic lineages. HSCs can reinitiate hematopoiesis for the life of a recipient. (See Fei et al., U.S. Pat. No. 5,635,387; McGlave et al., U.S. Pat. No. 5,460,964; Simmons et al., U.S. Pat. No. 5,677,136; Tsukamoto et al., U.S. Pat. No. 5,750,397; Schwartz et al., U.S. Pat. No. 759,793; DiGuisto et al., U.S. Pat. No. 5,681,599; Tsukamoto et al., U.S. Pat. No. 5,716,827; Hill et al., 1996.) Stem cells which differentiate only to form cells of the hematopoietic lineage, however, are unable to provide a source of cells for repair of other damaged tissues, for example, heart or lung tissue damaged by high-dose chemotherapeutic agents. They are also limited in their use in cell-based therapy to the correction of defects that affect only cells of the hematopoietic lineage. Similarly, their use in in vitro and/or ex vivo protein production is limited to proteins normally expressed in cells of hematopoietic lineage.

A second adult stem cell that has been studied extensively is the neural stem cell ("NSC") (Gage, 2000; Svendsen et al., 1999; Okabe et al., 1996). Several studies in rodents, and non-human primates and humans have shown that stem cells continue to be present in adult brain. These stem cells can proliferate in vivo and continuously regenerate at least some neuronal cells in vivo. When cultured ex vivo, NSCs can be induced to differentiate into different types of neurons and glial cells. Clarke et al. (2000) reported that NSCs from Lac-Z transgenic mice were able to contribute, not only to tissues of the central nervous system, but also to mesodermal derivatives and epithelial cells of the liver and intestine. They were not found in other tissues, including the hematopoietic system. These studies therefore suggested that adult NSCs may have significantly greater differentiation potential than previously realized, but still do not have the pluripotent capability of ES cells or of the adult derived multipotent adult stem cells (MASCs), also known as MAPCs, described in Furcht et al. (International Application Nos. PCT/US00/21387 and PCT/US02/04652) and herein.

A third tissue specific cell with stem cell properties is the mesenchymal stem cell ("MSC"), initially described by Fridenshtein (1982). MSC, originally derived from the embryonal mesoderm, can be isolated from adult bone marrow ("BM") and can differentiate to form muscle, bone, cartilage, fat, marrow stroma, and tendon. A number of MSCs have been isolated. (See, for example, Caplan et al., U.S. Pat. No. 5,486,359; Young et al., U.S. Pat. No. 5,827,735; Caplan et al., U.S. Pat. No. 5,811,094; Bruder et al., U.S. Pat. No. 5,736,396; Caplan et al., U.S. Pat. No. 5,837,539; Masinovsky, U.S. Pat. No. 5,837,670; Pittenger, U.S. Pat. No. 5,827,740; Jaiswal et al., 1997; Cassiede et al., 1996; Johnstone et al., 1998; Yoo et al., 1998; Gronthos, 1994).

Of the many MSCs that have been described, most have demonstrated limited differentiation potential, only forming cells generally considered to be of mesenchymal origin. One of the most multipotent MSC reported is the cell isolated by Pittenger et al., which is capable of differentiating to form a number of cell types of mesenchymal origin (Pittenger et al., 1999).

Other tissue-specific stem cells have been identified, including gastrointestinal stem cells (Potten 1998), epidermal stem cells (Watt, 1997), and hepatic stem cells, also termed oval cells (Alison et al., 1998).

MAPCs are distinct from these other types of stem cells. They can be culture-isolated from multiple sources, such as bone marrow, blood, muscle, brain, skin, fat, umbilical cord and placenta, and have the same morphology, phenotype, in vitro differentiation ability and a highly similar expressed gene profile as ES cells. (See, for example, Reyes and Verfaillie, 2001; Reyes et al., 2001; Jiang et al., 2002a; Jiang et al., 2002b.) MAPCs constitutively expresses oct4 and high levels of telomerase and are negative for CD44, MHC class I and MHC class II expression. One benefit of MAPCs, in terms of therapeutic applications, is that no teratomas are formed in vivo. Furthermore, MAPCs contribute to multiple organs upon transplantation.

Most presently available approaches of gene delivery make use of infectious vectors, such as retroviral vectors, which include the genetic material to be expressed. These approaches have limitations, such as the potential of generating replication-competent virus during vector production; recombination between the therapeutic virus and endogenous retroviral genomes, potentially generating infectious agents with novel cell specificities, host ranges, or increased virulence and cytotoxicity; limited cloning capacity in the retrovirus (which, inter alia, restricts therapeutic applicability) and short-lived in vivo expression of the product of interest.

Further, in most gene delivery systems, it is not possible to direct or target the donor DNA (i.e., the DNA being delivered to the cell, such as therapeutic DNA) to a preselected site in the genome. In fact, in the widely used retrovirus-mediated gene delivery system, retroviruses integrate randomly into independent chromosomal sites in millions to billions of cells. This mixture of infected cells is problematic in two senses: first, since integration site plays a role in the function of the donor DNA, each cell has a different level of function and, second, since the integration of donor DNA into the genome can trigger undesired events, such as the generation of tumorigenic cells, the likelihood of such events is dramatically increased when millions to billions of independent integrations occur.

The problems of populations consisting of large numbers of independent integrants might be avoided in two ways. First, a single cell with a random integration site can be propagated until sufficient numbers of the cloned cell are available for further use. The cells that make up this clonal population would all function identically. While this is theoretically possible, success rates for creating a clonal population from a single cell can be low and the number of passages required to amass a usable number of transfected cells can be deleterious. Alternatively, gene targeting can be used, wherein the donor DNA is introduced into a population of cells such that the DNA sequence integrates into a preselected site in the genome. In this case, all the cells function identically and the risk of a deleterious integration event is eliminated.

A number of approaches to gene targeting have been described including chimeroplasty (Bandyopadhyay et al., 1999), triple helix formation (Casey et al., 2001) and short-fragment homologous recombination (Goncz, et al., 2001), all of which may increase the rate of gene targeting. A preferred method of gene targeting by homologous recombination is that of Treco et al., described, for example, in the U.S. Pat. Nos. 6,270,989 and 5,641,670 or in Selden et al., U.S. Pat. No. 6,303,379.

Another alternative approach, based on AAV-mediated gene transfer and targeting, has been described (Inoue et al., 1999; Hirata et al., 2000; Hirata et al., 2002). AAV is a dependent parvovirus with a single-stranded linear DNA genome, from which vectors can be made by replacing the viral genes with foreign DNA between the cis-acting inverted terminal repeats. AAV vectors genetically alter cells by chromosomal integration of the vector genome at the site-specific integration locus of wild-type AAV located on human chromosome 19 (Carter et al., 2000; Inoue et al., 1999; Hirata et al., 2000; Hirata et al., 2002). The gene targeting rates produced by AAV vectors approach 1% at the single-copy HPRT locus in normal human cells, 3 to 4 logs higher than can typically be achieved in human cells with conventional gene targeting methods.

The use of gene targeting has been proposed in ES cell, germ cell and somatic cell systems. Germ cell gene targeting refers to the modification of sperm cells, egg cells, zygotes, or early stage embryos. From a practical standpoint, and due to ethical concerns, germ cell gene targeting is inappropriate for human use. ES cell gene targeting is also controversial, and the availability of ES cells for these purposes is severely limited. In somatic cell gene therapy, targeting somatic cells (e.g., fibroblasts, hepatocytes, or endothelial cells) are removed from a donor organism, cultured in vitro, transfected with the gene(s) of interest, characterized, and used for a desired purpose. However, the practical use of somatic cells is limited to conditions that affect only one cell type. Therefore, for example, an altered somatic cell cannot be induced to differentiate into cells of various tissue types. In addition, somatic cells are generally limited in their potential to propagate in vitro. Hence, an approach that overcomes the drawbacks and limitations of the currently available methods and provides safe, efficacious, long-term protein production and delivery would be valuable.

Historically, transfer (or introduction) of exogenous DNA into stem cells has been challenging, with most of the known transfection methods giving sub-optimal transfer rates. To achieve efficient gene targeting, a good transfer rate is necessary. Achieving high rates of transfer in stem cells has been hindered by the fact that optimal transfection occurs when cells are cultured at high density, while lower cell densities are required to maintain stem cells in an undifferentiated state. In order to effectively use genetically altered stem cells in protein expression, including therapeutic applications, a method is needed that will result in optimal transfer efficiency, for example, under conditions that support undifferentiated stem cells. Moreover, such methods would be ideally suited for use with adult stem cells having pluripotent capacity, such as MAPCs.

SUMMARY OF THE INVENTION

The ability to repair, alter, replace, delete or express desired nucleotide sequences in the genome of MAPCs would expand the potential usefulness of MAPCs in the in vitro, ex vivo, or in vivo expression of a gene of interest in order to arrive at a multitude of desired outcomes, such as nutritional and/or therapeutic protein production, non-protein gene expression (e.g. generation, up/down regulation, or knock-out/-in of ribozymes), as well as treatment of disease. Use of gene targeting in MAPCs can provide methods for altering gene expression (i.e., by increasing or decreasing the production of a gene product) not only to produce a novel or enhanced gene product, but also for investigation of gene expression patterns and/or gene function.

The invention provides a method of altering a first gene expression pattern in an isolated multipotent adult progenitor cell (MAPC), the method comprising:
   a) introducing into a MAPC an exogenous polynucleotide molecule, wherein the polynucleotide molecule comprises i) a targeting nucleotide sequence and ii) a donor nucleotide sequence; and
   b) culturing the MAPC under conditions sufficient to homologously recombine the exogenous polynucleotide molecule, such that a resultant MAPC has a second expression pattern;
wherein the introducing and culturing are done simultaneously or consecutively.

A preferred polynucleotide molecule is a DNA molecule. A preferred targeting and/or donor nucleotide sequence is DNA. Preferably, a targeting nucleotide sequence is homologous to a genomic DNA sequence of the MAPC. More preferably, a donor nucleotide sequence encodes a gene product not expressed by the MAPC, such that the second expression pattern includes the gene product.

Gene expression in the resultant MAPC can be turned on or off increased or decreased.

MAPCs can be isolated from a mammal, such as a mouse, a rat or a human. MAPCs can be isolated from a source including, but not limited to, bone marrow, blood, brain, muscle, skin, fat, umbilical cord and placenta.

The exogenous DNA sequence can be introduced via nucleoporation.

The method of altering a first gene expression pattern in an isolated multipotent adult progenitor cell (MAPC) can further comprise differentiating the MAPC after culturing under conditions sufficient to homologously recombine the exogenous polynucleotide molecule (preferably a DNA molecule). The MAPC can be differentiated to form a cell of a type including, but not limited to, osteoblast, chondrocyte, adipocyte, fibroblast, marrow stroma, skeletal muscle, smooth muscle, cardiac muscle, occular, endothelial, epithelial, hepatic, pancreatic, hematopoietic, glial, neuronal and oligodendrocyte cell types.

The preferred exogenous DNA molecule can comprise a DNA sequence encoding a selectable marker, such as an antibiotic resistance gene.

The invention further provides a method of making recombinant multipotent adult progenitor cells (MAPCs), the method comprising:
   a) culturing isolated MAPCs at low density;
   b) nucleoporating the MAPC in the presence of an exogenous DNA molecule, wherein the DNA molecule comprises i) a DNA sequence homologous to a genomic DNA sequence of the MAPC and ii) optionally a DNA sequence encoding a gene product; and
   c) culturing the MAPC under conditions sufficient to homologously recombine the exogenous DNA molecule.

Preferably, the MAPCs are cultured at about 500 cells/cm$^2$.

The gene product can be, but is not limited to, FANCA, FANCB, FANCC, FANCD1, FANCD2, FANCE, FANCF, FANCG, hemoglobin, factor VIII, factor IX, erythropoietin, CFTR, collagen I, alpha 1 anti-trypsin, gamma-C, Rag1, Rag2, adenosine deaminase, phenylalanine hydroxylase, fumarate dehydroxylase, LDL receptor, aL-iduronidase and b-glucuronidase. Preferably, the gene product is FANCC.

The method of making recombinant multipotent adult progenitor cells can further comprise selecting the resultant MAPCs expressing the gene product.

The preferred exogenous DNA molecule can be a vector, such as a plasmid. The vector can further comprise a DNA sequence encoding a selectable marker, such as an antibiotic resistance gene.

The invention further provides a method of correcting a genetic defect in a mammal, wherein the defect is one or more defective nucleotide sequence(s) from which a functional gene product cannot be expressed, the method comprising:
   a) isolating a MAPC from the mammal having the genetic defect;
   b) introducing into the MAPC an exogenous DNA molecule, wherein the DNA molecule comprises i) a DNA sequence homologous to a genomic DNA sequence of the MAPC and ii) one or more non-defective nucleotide sequence(s) corresponding to the defective nucleotide sequence(s),
   c) culturing the MAPC under conditions sufficient to homologously recombine the exogenous DNA molecule into the genome of the MAPC, wherein the MAPC expresses the functional gene product;
   d) selecting MAPCs that express the functional gene product; and
   e) transplanting the MAPCs into the mammal.

The genetic defect can affect a gene encoding, for example, FANCA, FANCB, FANCC, FANCD1, FANCD2, FANCE, FANCF, FANCG, hemoglobin, factor VIII, factor IX, erythropoietin, CFTR, collagen I, alpha 1 anti-trypsin, gamma-C, Rag1, Rag2, adenosine deaminase, phenylalanine hydroxylase, fumarate dehydroxylase, LDL receptor, aL-iduronidase and b-glucuronidase.

Selection can be carried out by treatment of the MAPCs with a dose of mitomycin C, wherein the dose is toxic to MAPCs not expressing the gene product and non-toxic to MAPCs expressing the gene product.

The method of correcting a genetic defect can further comprise differentiating the MAPCs. The differentiating can be done after culturing under conditions sufficient to homologously recombine the exogenous DNA molecule and optionally, before transplanting the MAPCs into the mammal.

The exogenous DNA molecule can further comprise a DNA sequence encoding a selectable marker, such as an antibiotic resistance gene. Thus, the method of correcting a genetic defect can further comprise selecting MAPCs expressing the selectable marker after culturing under conditions sufficient to homologously recombine the exogenous DNA molecule.

Preferably, the sequence encoding the selectable marker can be exised from the genome of a resultant MAPC. Most preferably, the sequence encoding the selectable marker is flanked at each of the 5' and 3' ends by a lox P site. Thus, the method of correcting a genetic defect can further comprise selecting MAPCs expressing the selectable marker after culture under conditions sufficient to homologously recombine the exogenous DNA molecule and introducing into the MAPCs a vector comprising a gene encoding Cre, such that Cre is expressed and the selectable marker is excised. In a preferred embodiment, the selectable marker is excised before transplanting the MAPCs into the mammal.

The vector comprising a gene encoding Cre can be an adeno-associated viral vector.

The method of correcting a genetic defect can further comprise selecting MAPCs expressing the selectable marker after culturing under conditions sufficient to homologously recombine the exogenous DNA molecule and introducing into the MAPCs a TaT-Cre fusion protein, such that the selectable marker is excised. In a preferred embodiment, the selectable marker is excised before transplanting the MAPCs into the mammal.

The invention further provides a MAPC, or the differentiated progeny thereof, isolated from a mammal with a genetic defect, wherein the defect is one or more defective nucleotide sequence(s) at a known locus such that a functional gene product is not expressed, and wherein the MAPC comprises a DNA molecule with one or more non-defective nucleotide sequence(s) corresponding to the known locus, and the MAPC expresses the functional gene product.

The invention further provides a method of expressing a functional gene product in an isolated MAPC having a defective nucleotide sequence from which a functional gene product cannot be expressed, the method comprising:
a) introducing into the MAPC an exogenous DNA molecule, wherein the DNA molecule comprises i) a DNA sequence homologous to a genomic DNA sequence of the MAPC and ii) a non-defective nucleotide sequence corresponding to the defective nucleotide sequence; and
b) culturing the MAPC under conditions sufficient to homologously recombine the exogenous DNA molecule into the genome of the MAPC, wherein the MAPC expresses the functional gene product.

In a preferred embodiment, the defective nucleotide sequence is in FANCC.

The method of expressing a functional gene product in an isolated MAPC can further comprise selecting the MAPCs that express the functional gene product.

The invention further comprises a recombinant MAPC produced by the methods of the invention.

The term "comprising" in this disclosure can mean "including" or can have the meaning commonly given to the term "comprising" in U.S. Patent Law.

Other aspects of the invention are described in or are obvious from (and within the ambit of the invention) the following disclosure.

BRIEF DESCRIPTION OF DRAWINGS

The following Detailed Description, given by way of example, but not intended to limit the invention to specific embodiments described, may be understood in conjunction with the accompanying drawings, incorporated herein by reference, in which:

FIG. 8 shows the nucleotide sequence of the human FANCC cDNA (SEQ ID NO:1).

FIG. 9 shows the amino acid sequence of the human FANCC protein (SEQ ID NO:2).

DETAILED DESCRIPTION OF THE INVENTION

Figure 1:
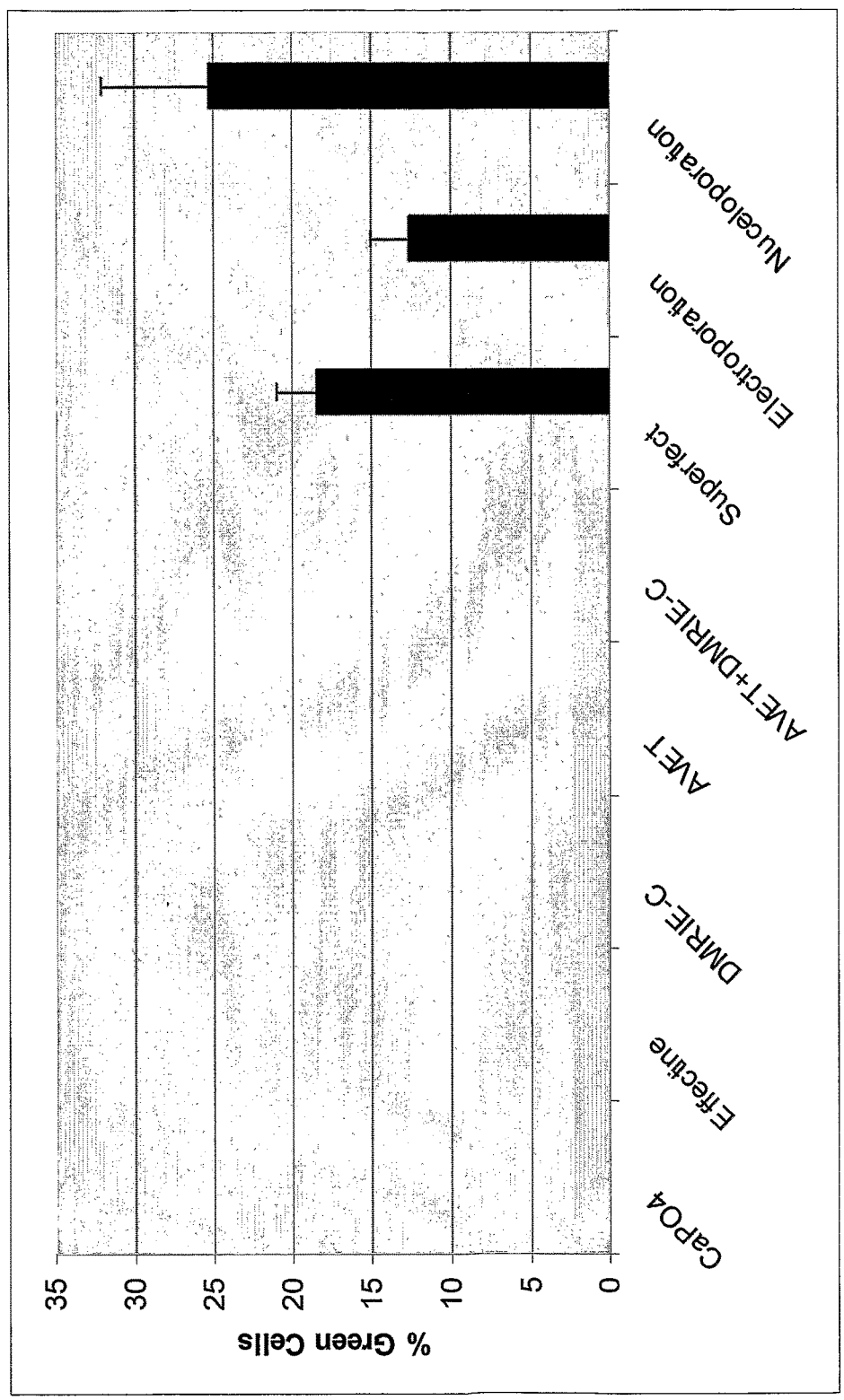
FIG. 1 shows the percentage of cells expressing GFP after transfection using various methods.

As described herein, MAPC technology, in combination with homologous recombination, provides a powerful tool for altering gene expression to produce a gene product in vitro, to determine the function of a gene and to treat diseases and conditions caused by abnormal gene function. The methods and cells of the present invention can be used for a wide variety of purposes. The methods can be used to alter MAPCs in order to repair, alter, delete or replace DNA already present in the MAPC, to activate/knock in a gene or to add or replace regulatory sequences to a MAPC, to knock out or remove an entire gene or gene portion present in MAPCs, or to introduce a gene or DNA sequence into a MAPC, at a preselected site, which encodes a therapeutic product or other desired product.

Accordingly, the invention provides a method of altering a first gene expression pattern in an isolated multipotent adult progenitor cell (MAPC), the method comprising:
(a) introducing into the MAPC an exogenous polynucleotide molecule, wherein the polynucleotide molecule comprises i) a targeting necleotide sequence which includes a sequence homologous to a genomic nucleotide sequence of the MAPC and ii) a donor nucleotide sequence; and
(b) culturing the MAPC under conditions sufficient to homologously recombine the exogenous polynucleotide molecule, such that a resultant MAPC has a second gene expression pattern different than said first gene expression pattern.

MAPCs can be isolated from a mammal such as a mouse, a rat or a human. MAPCs can be isolated from a source including, but not limited to, bone marrow, blood, brain, muscle, skin, fat, umbilical cord and placenta.

As used herein, the term "isolated" as used in "isolated MAPC," or "isolated MAPCs" refers to one or more MAPCs harvested from a source. A preferred method of harvesting a MAPC is described in PCT/US00/21387 (published as WO 01/11011) and PCT/US02/04652 (published as WO 02/064748); MAPC compositions and the methods for the isolation thereof are incorporated herein by reference.

In general, "homologous recombination" is the substitution of a segment of DNA by another that is identical or nearly so. As used herein, to homologously recombine an exogenous DNA molecule is to physically exchange segments of the molecule, preferably segments flanking the donor nucleotide sequence, with homologous genomic DNA sequences of the MAPC, such that the exogenous DNA molecule, or a portion thereof, is inserted into the MAPC genome. For a review of homologous recombination, see Lewin, B., Genes V, Oxford University Press, New York, 1994, pp. 968-997; and Capecchi, M., (1989) Science 244: 1288-1292; Capecchi, M., (1989) Trends Genet. 5(3):70-76.

As used herein, an "exogenous polynucleotide molecule," can comprise a polynucleotide sequence obtained from a source other than the very cell into which it is introduced.

The polynucleotide can comprise a sequence of synthetic or naturally occurring DNA or RNA nucleotide bases.

As used herein, a "targeting nucleotide sequence," is a sequence that shares homology with a genomic sequence(s) of the MAPC. For example, where gene activation is desired (e.g., when the donor sequence comprises a transcriptional regulatory sequence, such as a transcriptional activation or enhancer sequence), the targeting nucleotide sequence can have homology with a genomic sequence within the gene to be activated or upstream of the gene to be activated, the upstream region being up to and including the first functional splice acceptor site on the same coding strand of the gene of interest, and by means of which homology the donor sequence that activates the gene of interest is integrated into the genome of the cell containing the gene to be activated. Where insertion of a donor sequence into a coding region of a gene is desired, the targeting nucleotide sequence can share homology with a genomic sequence, preferably, in an exon of that gene. Where insertion of a donor sequence into a non-coding region is desired (e.g., insertion of a donor sequence without interfering with transcription of endogenous genes is desired), the targeting nucleotide sequence can share homology with a genomic sequence that is, preferably, not located within a transcribed genomic locus. A "genomic locus" refers to a particular location within the genome (e.g., the location of a gene).

As used herein, a "donor nucleotide sequence" is any nucleotide sequence that is intended to be inserted into the MAPC genome regardless of its size. The donor nucleotide sequence can comprise, for example, a coding sequence, or a portion thereof, a transcriptional regulatory sequence, such as a transcriptional activation, enhancer or silencer sequence, or a non-coding sequence, such as a knock-out cassette, as well as a single nucleotide.

In general, in the various methodologies of the present invention, preferably, the polynucleotide molecule is DNA; and the exogenous polynucleotide molecule is contained in a vector. Moreover, the targeting and the donor nucleotide sequence of the exogenous polynucleotide molecule may be one and the same.

Introduction into the MAPC of an exogenous polynucleotide molecule, preferably a DNA molecule, can be through any methodology, such as transfection, liposome fusion or electroporation. Preferably, introduction into the MAPC of the exogenous polynucleotide molecule is carried out through nucleoporation.

Gene expression in the resultant MAPC can be turned on, increased, turned off or decreased. The methods of the invention can result in addition, deletion or replacement of all or part of a gene in a MAPC. Such manipulation of the genome is useful in several respects. The method is particularly useful to turn on or increase expression of a gene that is present in a MAPC, but is not expressed at all or in biologically significant levels (i.e. such that a functional gene product is produced). Once gene expression is altered, for example, turned on or increased, the resultant MAPC can be used to produce the gene product (i.e., protein or RNA molecule) in vitro or in vivo. The suppression of gene expression can be useful in determining the function of a gene product, or in gene mapping as well as correcting a genetic defect. In addition, when a gene product is not expressed, or is expressed in a reduced amount, the relative overexpression of other gene products can be simulated. Such techniques can be useful, for example, in the generation of disease models, such as cancer.

The resultant MAPC, having the second gene expression pattern, can be selected on that basis. Accordingly, the invention further provides a method of identifying a homologously recombined multipotent adult progenitor cell (MAPC) by selecting for an effect of the donor nucleotide on said MAPC. Thus, recombinant MAPCs produced by the above methods are also provided by the invention.

As used herein, a "recombinant MAPC," is a MAPC comprising a donor nucleotide sequence inserted into its genome. As used herein, a "genetically altered MAPC" is a MAPC whose genome is altered, as a result of homologous recombination, by at least one nucleotide deletion, substitution, addition. "Substitution" can include the exchange of a genomic nucleotide base(s) for either the same or a different nucleotide base(s) of an exogenous polynucleotide molecule (e.g., a genomic guanine exchanged for an exogenous guanine or a genomic guanine exchanged for an exogenous thymine).

In a preferred embodiment, the invention provides a method of making a recombinant multipotent adult progenitor cell (MAPC), comprising:
(a) culturing MAPCs;
(b) nucleoporating the MAPC in the presence of an exogenous DNA molecule, wherein the DNA molecule comprises i) a DNA sequence homologous to a genomic DNA sequence of the MAPC and ii) optionally a DNA sequence encoding a gene product; and
(c) culturing the MAPC obtained in (b) under conditions sufficient to homologously recombine the exogenous DNA molecule, thereby making a recombinant MAPC.

In a preferred embodiment of the above method, the MAPCs of (a) and/or (c) are cultured at low density, preferably at about 500 cells/cm$^2$.

In another embodiment, the invention provides a method of introducing a nucleotide of interest ("NOI") into multipotent adult progenitor cells (MAPCs) comprising:
(a) culturing MAPCs at low density, preferably at about 500 cells/cm$^2$;
(b) introducing a vector comprising a nucleotide of interest ("NOI") into the MAPCs using nucleoporation.

Frequently, a genetic disorder or disease results from error(s) in the genetic code in an organism's genome, wherein a mutation of one or more nucleotides causes alteration(s) in the gene expression, such as over or under expression, activation or deactivation of a gene. As used herein "genetic code" refers to a sequence of nucleotides, coded in triplets ("codons") along an RNA sequence.

Errors in the genetic code can occur in one or more gene loci, within or outside a coding and/or regulatory region. A single nucleotide mutation can alone or cumulatively (and/or synergistically) with one or more single nucleotide mutation give rise to a disease or disorder in the whole cell, tissue and/or organism. For example, mutations in genes affecting a protein function such as anemia, diabetes, hepatitis, hemophilia, hemoglobinopathies, muscular dystrophy and cystic fibrosis, to name a few, could be corrected by methods of the invention.

For such conditions, the invention further provides a method of correcting a genetic defect in a mammal, wherein the defect is one or more defective nucleotide sequence(s) in the genome of the mammal that give rise to defective gene expression, the method comprising:
(a) culturing a MAPC from the mammal having the genetic defect;
(b) introducing into the MAPC an exogenous DNA molecule, wherein the DNA molecule comprises i) a targeting DNA sequence homologous to a genomic DNA sequence of the MAPC and ii) one or more donor nucleotide sequence(s) necessary for correcting said genetic defect in said mammal;

(c) culturing the MAPC under conditions sufficient to homologously recombine the exogenous DNA molecule into the genome of the MAPC, thereby obtaining a genetically altered MAPC;

(d) selecting said genetically altered MAPC; and (e) transplanting said genetically altered MAPC into the mammal, wherein the selecting recited in (d) and the transplanting recited in (e) can be done in any order or simultaneously.

Preferably, the exogenous DNA molecule is contained in a "correction vector." As used herein, a "correction vector" is comprised of a replicon (i.e., a polynucleotide molecule capable of independently replicating, such as a plasmid or viral backbone), that contains an exogenous polynucleotide molecule having i) a targeting nucleotide sequence and ii) one or more donor nucleotide sequence(s). Prior to introduction into a MAPC of interest, the correction vector can be linearized at a site, preferably, outside the targeting nucleotide sequence or the donor nucleotide sequence. Preferably, the sequence homology between the genomic nucleotide sequence of the MAPC and the targeting nucleotide sequence includes either a region from within or proximal to the genomic locus of the genetic defect.

Another preferred embodiment involves a method of expressing a functional gene product in an isolated MAPC having a defective genetic code from which a functional gene product cannot be expressed, said method comprising:

(a) introducing into the MAPC an exogenous DNA molecule, wherein the DNA molecule comprises i) a targeting DNA sequence homologous to a genomic DNA sequence of the MAPC and ii) a donor nucleotide sequence corresponding to the defective genetic code; and (b) culturing the MAPC under conditions sufficient to homologously recombine the exogenous DNA molecule into the genome of the MAPC, wherein the MAPC expresses the functional gene product.

In addition to the instances when undifferentiated recombinant MAPCs are administered to a patient and then differentiated into specific cells in vivo, the progeny of the recombinant MAPCs can be differentiated ex vivo before, after, or concurrent with selection and then be administered to provide a desired, e.g., a therapeutic, benefit. The differentiated cells may be administered as a mixture of non-homogenous cells (i.e., cells at various stages of differentiation and/or in admixture with one or more different kind(s) of cells) or as cells of various degrees of purity/homogeneity in type and stage of development. The cells can be differentiated to form osteoblasts, chondrocytes, adipocytes, fibroblasts, marrow stroma, skeletal muscle cells, smooth muscle cells, cardiac muscle cells, ocular cells, endothelial cells, epithelial cells, hepatic cells, pancreatic cells, hematopoietic cells, glial cells, neuronal cells, oligodendrocytes, or any other type of specialized cell.

In a preferred embodiment, the MAPC is isolated from a mammal, such as a mouse, a rat, a human or other primate, as well as a dog or pig. Most preferably the MAPC is isolated from a human.

MAPCs can be isolated from most organ, tissue and fluid sources, including, but not limited to, BM, blood, brain, heart, muscle, skin, fat, umbilical cord and placenta. In a preferred embodiment, MAPCs are isolated from BM, brain, heart or muscle. In an especially preferred embodiment, MAPCs are isolated from BM, heart or muscle.

The exogenous DNA molecule can be introduced into the MAPC in a vector, or correction vector, which can be any vector comprising a polynucleotide sequence, e.g. a plasmid vector or a viral vector. In a preferred embodiment, it is a plasmid. The vector can further comprise a DNA sequence encoding a selectable marker, optionally flanked at the 5' and 3' ends by lox P sites. The selectable marker is preferably an antibiotic resistance gene. In this embodiment, the methods of the invention can further comprise the step of selecting cells expressing the selectable marker prior to selecting cells expressing the gene product or protein. The methods of the invention can also further comprise introducing the Cre enzyme into the cells prior to transplantation, such that the selectable marker is removed from the genome. Cre can be introduced in any manner, preferably, either by transfection of the cells with a vector comprising the cre gene, or by crosslinking the polypeptide to the HIV trans-activating transduction (Tat) peptide and introducing it into the cells.

Selection of homologously recombined cells can be in vitro, prior to transplantation of the cells, and/or in vivo, e.g., after transplantation has occurred. In vivo selection can be by administration of a drug to which untransfected cells are susceptible, such as mitomycin C, or it can be by means of determining expression of a functional gene product by methods known in the art. Phenotypic selection, for example by histological analysis or by the reduction of symptoms manifested by the genetic defect, may also be used as a criterion. The preferred dose of mitomycin C for in vivo selection is between about 0.3 mg/kg/week and 1 mg/kg/week.

The invention further provides a MAPC isolated from a mammal with a genetic defect, the defect arising from mutation of one or more nucleotide(s) on the mammal's genome. The mutation is, for example, responsible for inability of the cell to express a sequence(s) from which a functional gene product can be expressed. The MAPC of the present invention comprises a genetically altered MAPC containing an exogenous polynucleotide molecule, such as a DNA molecule, wherein the polynucleotide molecule comprises i) a targeting polynucleotide sequence homologous to a genomic DNA sequence of the MAPC and ii) one or more donor nucleotide sequence(s) necessary for correcting the genetic defect. In a preferred embodiment, the targeting and/or donor nucleotide sequences are DNA and correspond to the defective nucleotide sequence(s) at the gene locus responsible for the genetic defect, such that the exogenous DNA molecule is integrated into the genome of the cell and the cell expresses the functional gene product. A differentiated cell derived from this genetically altered MAPC is also provided by the invention. The differentiated cell can be an osteoblast, chondrocyte, adipocyte, fibroblast, marrow stroma, skeletal muscle, smooth muscle, cardiac muscle, ocular, endothelial, epithelial, hepatic, pancreatic, hematopoietic, glial, neuronal, oligodendrocyte, or any other type of differentiated cell.

The present invention is useful for conducting targeted gene therapy in multipotent adult progenitor cells (MAPCs) from a mammal, preferably a human, other primates, mouse, rat, dog, and pig, to produce therapeutic gene products in a wide variety of cell and tissue types. A contemplated application of this technology is the method of correcting a genetic defect in a mammal by administering a therapeutically effective amount of the genetically altered MAPCs or their progeny. The methods of the invention can be used to treat any disease or condition caused by a genetic deficiency in a known gene, including metabolic diseases, storage diseases, muscular dystrophy, osteogenesis imperfecta, severe combined immunodeficiency, liver disease, diabetes, hepatitis, hemophilia, hemoglobinopathies, anemia, and cystic fibrosis. An unexpected benefit of this approach is that the need for pretreatment and/or post treatment of the patient with irradiation, chemotherapy, immunosuppressive agents or other drugs or treatments is reduced or eliminated. The induction of tolerance before or during treatment is also not required, however, allogenic application is within the scope of the invention.

Another application of the invention is to provide a method for stably transfecting MAPCs under conditions that result in efficient transfection rates at cell densities that are sufficiently low to maintain MAPCs in an undifferentiated state.

MAPCs can be derived from a non-embryonic organ, tissue or fluid, and have the capacity to differentiate to form cell types of mesodermal, ectodermal and endodermal origin. Differentiation can be induced in vivo or ex vivo, to produce a population of MAPC progeny. The progeny can have the capacity to be further differentiated, or can be terminally differentiated.

The invention, preferably, provides a method of altering a first gene expression pattern in an isolated multipotent adult progenitor cell (MAPC), the method comprising:
(a) introducing into the MAPC an exogenous DNA molecule, wherein the DNA molecule comprises i) a targeting DNA sequence homologous to a genomic DNA sequence of the MAPC and ii) a donor DNA sequence encoding a gene product not normally expressed by the MAPC; and
(b) culturing the MAPC under conditions sufficient to homologously recombine the exogenous DNA molecule into the genome of said MAPC, such that a resultant MAPC has a second gene expression pattern that includes the gene product.

The targeting DNA sequence and the donor DNA sequence can be one and the same or different.

Preferred methods of MAPC isolation are described in PCT/US00/21387 (published as WO 01/11011) and PCT/US02/04652 (published as WO 02/064748), and these methods are incorporated herein by reference. MAPCs can be isolated from multiple sources, including bone marrow, muscle, brain, spinal cord, blood or skin. To isolate MAPCs, bone marrow mononuclear cells can be derived from bone marrow aspirates, which can be obtained by standard means known to those of skill in the art (see, for example, Muschler, G. F., et al., J. Bone Joint Surg. Am. (1997) 79(11): 1699-709, Batinic, D., et al., Bone Marrow Transplant. (1990) 6(2): 103-7).

MAPCs are present within the bone marrow (or other organs, such as liver and brain), but do not express the common leukocyte antigen CD45 or erythroblast specific glycophorin-A (GlyA). The mixed population of cells can be subjected to a Ficoll Hypaque separation. Cells can then be subjected to negative selection using anti-CD45 and anti-Gly-A antibodies, depleting the population of CD45$^+$ and GlyA$^+$ cells, and recovering the remaining approximately 0.1% of marrow mononuclear cells. Cells can also be plated in fibronectin coated wells and cultured as described below for 2-4 weeks after which the cells are depleted of CD45$^+$ and GlyA$^+$ cells. Alternatively, positive selection can be employed to isolate cells using a combination of cell-specific markers, such as the leukemia inhibitory factor (LIF) receptor. Both positive and negative selection techniques are known to those of skill in the art, and numerous monoclonal and polyclonal antibodies suitable for negative selection purposes are also known in the art (see, for example, LeukocZe Typing V, Schlossman, et al., Eds. (1995) Oxford University Press) and are commercially available from a number of sources.

Preferable ranges of homogeneity in populations comprising MAPCs are 50-55%, 55-60%, and 65-70%. More preferably the homogeneity is 70-75%, 75-80%, 80-85%; and most preferably the homogeneity is 85-90%, 90-95%, and 95-100%. Homogeneity of MAPCs can be determined according to the cell surface marker profile within a population.

Gene expression in the resultant MAPC of the methods of present invention is turned on, increased, turned off or decreased. By a "expression pattern" is meant the structure of and approximate amount of a gene product that is produced by a cell under specific conditions. Expression patterns can be determined by any methods known in the art, for example, by quantitative Western blot, amino acid sequence analysis, and/or protein concentration assays. "Normally expressed" refers to the structure of and approximate amount of a gene product that is produced by a cell, under specific conditions, that does not have a genetic defect in the nucleotide sequence encoding the gene product. "Gene product" as used herein and commonly understood in the art refers to a nucleic acid molecule (such as RNA) and/or a peptide or polypeptide encoded by the gene of interest.

"Conditions suitable for homologous recombination" include cell culture conditions whereby cells are plated at a density and in a medium that allows cells to be grown without differentiation during the recombination event. One example of suitable culture conditions would be $5 \times 10^3$ MAPCs in 200 µL medium comprising 58% DMEM-LG, 40% MCDB-201 (Sigma Chemical Co, St Louis, Mo.), supplemented with 1× insulin-transferrin-selenium (ITS), 1× linoleic-acid bovine serum albumin (LA-BSA), $10^{-8}$ Dexamethasone, $10^{-4}$ M ascorbic acid 2-phosphate (all from Sigma), 100 U penicillin and 1,000 U streptomycin (Gibco) and 0-10% fetal calf serum (FCS) (Hyclone Laboratories, Logan, Utah) with 10 ng/ml of EGF (Sigma) and 10 ng/ml PDGF-BB (R&D Systems, Minneapolis, Minn.). For detailed protocols, see Hatada at el. (2001) and Yanez and Porter ACG (1999).

Following homologous recombination, cells containing a donor nucleotide sequence can be selected in culture. The length of selection will vary, depending on the selectable marker, or combination of selectable markers, used. Selectable marker genes which can be used include, but are not limited to neo, gpt, dhfr, ada, pac, hyg, mdrl, hisD, HSVTK and blastocidin. The selectable marker is preferably an antibiotic resistance gene. Most preferably, the hygromycin resistance (Hyg$^R$) gene is used as a selectable marker gene, and cells containing Hyg$^R$ are cultured for at least 24 hours, up to about 7 days, most preferably for about 2 days to about 5 days, in the presence of hygromycin. Where more than one selectable marker gene is used, a second round of selection can be carried out using, for example, the selectable marker genes neomycin, HSVTK and blastocidin. Thus, after the initial time for selection (e.g., 24 hours to about 7 days) a second period of selection can be carried out according to the selectable marker gene of choice. For example, selection for neomycin resistance can be performed for about 7 to about 14 days, while HSVTK and blastocidin resistance can be performed for about 5 to about 7 days. It is well within the skill in the art to vary the duration of selection for a particular selectable marker gene according to the time known in the art to be effective for selection.

Where the selectable marker gene is homologously recombined into the HPRT locus, endogenous HPRT is disrupted and cells are no longer sensitive to media containing 6-thioguanine (6-TG). One example of a dual selection method which employs both 6-thioguanine (6-TG) and Hyg$^R$ selection is provided in Example 6. Other examples can be found in the art.

In a preferred embodiment, the invention provides a method of introducing a nucleotide of interest ("NOI") into multipotent adult progenitor cells (MAPCs) comprising the steps of:
  (a) culturing isolated MAPCs at low density, preferably at about 500 cells/cm$^2$;
  (b) introducing a vector comprising a nucleotide of interest ("NOI") into the MAPCs using nucleoporation.

Introduction of the vector can be carried out by any method, including, but not limited to, liposome fusion, electroporation, or nucleoporation. Nucleoporation is the preferred mode of transfection, as this method is believed to allow high transfection efficiencies at low cell densities. Nucleoporation solves the paradox faced in the transfection of MAPCs: the rate of transfection must be high enough to produce a sufficiently large population of genetically altered cells to use in therapeutic applications, but the density of MAPCs in culture must be low enough to prevent differentiation and loss of multipotency.

A "nucleotide of interest" (NOI) can be any nucleic acid sequence, which need not necessarily be a complete naturally occurring DNA or RNA sequence. Thus, the NOI can be, for example, a synthetic RNA/DNA sequence, a recombinant RNA/DNA sequence (i.e. prepared by use of recombinant DNA techniques), a cDNA sequence or a partial genomic DNA sequence, including combinations thereof. The sequence need not be a coding region. If it is a coding region, it need not be an entire coding region. In addition, the RNA/DNA sequence can be in a sense orientation or in an anti-sense orientation. Preferably, it is in a sense orientation. Preferably, the sequence is, comprises, or is transcribed from cDNA. The NOI can be useful for assay development, protein production, therapeutic or diagnostic applications.

"Low density" refers to cell densities of about 0.5-1.5× $10^3$ cell/cm$^2$, preferably about 1.0×$10^3$ cell/cm$^2$, and even more preferably about 0.5-2.0×$10^3$ cell/cm$^2$. most preferably, a "low density" refers to a cell density of 0.5×$10^3$ cell/cm$^2$. Advantageously, the transfection efficiency is at least about 15%, preferably at least about 20%, and most preferably at least about 25% at 24 hours post-transfection, and at least about 20%, preferably at least about 25%, more preferably at least about 30% and most preferably at least about 35% at 48 hours post transfection.

In a preferred embodiment, the invention further provides a method of correcting a genetic defect in a mammal, wherein the defect is one or more defective nucleotide sequence(s) from which a functional gene product cannot be expressed, the method comprising:
  (a) isolating a MAPC from the mammal having the genetic defect;
  (b) introducing into the MAPC an exogenous DNA molecule, wherein the DNA molecule comprises i) a DNA sequence homologous to a genomic DNA sequence of the MAPC and ii) one or more non-defective nucleotide sequence(s) corresponding to the defective nucleotide sequence(s);
  (c) culturing the MAPC under conditions sufficient to homologously recombine the exogenous DNA molecule into the genome of the MAPC, wherein the MAPC expresses the functional gene product;
  (d) selecting MAPCs that express the functional gene product; and
  (e) transplanting the MAPCs into the mammal,
    wherein d) and e) can be done in any order or simultaneously. For example, MAPCs expressing the functional gene product can be selected in vitro, using any selectable marker known in the art, and then transplanted into the mammal. Or, the genetically altered MAPCs can be transplanted into the mammal and the selection can be performed in vivo, for example, via antibiotic selection.

For purposes of this invention, a "genetic defect", "genetic deficiency" or "defective nucleotide sequence" refer to the presence of at least one mutation, i.e., deletion, addition, or substitution of one or more nucleic acid(s) in a DNA sequence encoding a gene product, including any promoter and regulatory sequences, wherein a functional gene product (nucleic acid and/or protein) is not expressed. A "non-defective nucleotide sequence" comprises at least part of a gene which encodes a functional gene product. A "corrected cell" is a cell in which a genetic defect has been corrected by incorporation of a non-defective nucleotide sequence into the cell's genome by homologous recombination.

DNA incorporated into MAPCs can be an entire gene encoding an entire desired product or a gene portion which encodes, for example, the active, functional or defective portion(s) of the gene product. The DNA can be obtained from a source in which it occurs in nature or can be produced, using genetic engineering techniques or synthetic processes. After transfection into MAPCs, the non-defective nucleotide sequence is stably incorporated into the cell's genome.

Tissue specific expression of the gene product can occur, as the homologously recombined nucleotide sequence will be under the control of the endogenous gene promoter by virtue of its locus of integration. For example, a sequence encoding insulin would be produced in islet cells, hemoglobin would be produced in erythroid progenitor cells, erythropoietin in kidney epithelial cells and liver hepatocytes, etc.

A vector, more specifically, a correction vector, which includes the non-defective nucleotide sequence and additional sequences, such as sequences necessary for expression and/or integration of the nucleotide sequence, can be used. Any type of vector known in the art may be used, including, but not limited to, retroviral vectors, adenoviral vectors, adeno-associated viral vectors, other DNA virus-based vectors (such as herpes simplex virus), and non-viral plasmid vectors. In a preferred embodiment, the vector is a plasmid.

The total length of the DNA molecule in the correction vector will vary according to the number of components (non-defective nucleotide sequence, selectable marker gene, etc.) and the length of each. It will also vary depending upon the nature of the genetic defect in a given individual. The nature of the genetic defect can routinely be determined by the skilled artisan using methods known in the art. Once the nature of the genetic defect is known, vectors can be designed based on the site and the extent of the mutation in an individual. In general, a correction vector can include a non-defective version of the defective nucleotide sequence, along with homologies to sequences upstream and/or downstream of the defective sequence. The length of the donor non-defective sequence varies with the specific genetic defect. As small as a single nucleotide mutation may cause a genetic defect. Therefore, the length of the donor DNA used to correct the defect can be decided based on the preferences of choice and design. For example, to correct a single nucleutide mutation, a donor fragment should at least include the correct nucleotide corresponding to the mutated or defective nucleic acid. For example, a donor fragment of 10-20 base pairs spanning the 5' and 3' region surrounding the mutation can be employed. Yet, an even larger or smaller fragment could be used in a given situation. However, generally the length of the donor DNA is at least about 20 nucleotides. Preferably, the length is between about 20 and 500 nucleotides. The length of the upstream and/or downstream homologous sequences (the targeting DNA) is preferably at least about 1000 nucleotides, more preferably between about 2000 to about 3,000 nucleotides, and most preferably between about 3000 to about 5,000 nucleotides, but again, its actual length in a given situation can be decided based on experimental choice and design. The goal of the design of the DNA molecule is to have sufficient homology with genomic DNA to undergo homologous recombination, and thus it serves to target integration into genomic DNA such that additional targeting sequences are unnecessary.

Stably transfected cells are selected and cultured to propagate a sufficient population of cells for transplantation. Recombinant MAPCs can be administered to a subject by a variety of methods known in the art. Preferably, administration is through injection, including but not limited to, transvascular injection, intramuscular injection, and intravenous injection.

Intravenous injection is the simplest method of cell administration, however a greater degree of dependence on homing of the MAPCs is required for them to reach a tissue of interest. Hence, if necessary, the MAPCs can be directly injected (or otherwise transplanted) into the tissue(s) of interest. Carefully controlled dosing, which is readily determined by one skilled in the art, enhances this method of administration.

A method to potentially increase cell survival is to incorporate recombinant MAPCs into a biopolymer or synthetic polymer. Depending on the patient's condition, the site of injection might prove inhospitable for cell seeding and growth because of scarring or other impediments. Examples of biopolymer include, but are not limited to, cells mixed with fibronectin, fibin, fibrinogen, thrombin, collagen, and proteoglycans. This could be constructed with or without included cytokines or differentiation factors. Additionally, these could be in suspension but residence time at sites subjected to flow would be nominal. Another alternative is a three-dimension gel with cells entrapped within the interstices of the cell biopolymer admixture. Again differentiation factors or cytokines could be included with the cells. These could be deployed by injection via various routes described herein, via cardiac catheters, or other surgical procedures.

An issue concerning the therapeutic use of stem cells, in general, is the quantity of cells necessary to achieve an optimal effect. Preferably, approximately $1\times10^6$ recombinant MAPCs are transplanted into the mammal. In current human studies of autologous mononuclear bone marrow cells, empirical doses ranging from 1 to $4\times10^7$ cells have been used with encouraging results. However, different scenarios may require optimization of the amount of cells injected into a tissue of interest. Thus, the quantity of cells to be administered will vary for the subject being treated. The precise determination of what would be considered an effective dose may be based on factors individual to each patient, including their size, age, size of the infarct or other tissue damage, and amount of time since the damage occurred. Therefore, dosages can be readily ascertained by those skilled in the art from this disclosure and the knowledge in the art.

The skilled artisan can readily determine the amount of cells and optional additives, vehicles, and/or carrier in compositions and to be administered in methods of the invention. Typically, any additives (in addition to the active stem cell(s) and/or cytokine(s)) are present in an amount of 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations are routine in the art and can be readily ascertained from the present disclosure and the documents cited herein. Similarly, the timing of sequential administrations can be routinely ascertained by the skilled artisans.

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used is compatible with the cells and readily ascertained by the skilled artisans.

Sterile injectable solutions (and suspensions) can be prepared by incorporating the cells utilized in practicing the present invention in the required amount of the appropriate liquid preparation, optionally containing various amounts of other ingredients, as desired.

In one embodiment, recombinant MAPCs can be administered initially, and thereafter maintained by further administration of recombinant MAPCs. For instance, recombinant MAPCs can be administered by one method of injection, and thereafter further administered by a different or the same type of method. The patient's levels can then be maintained, for example, by intravenous injection, although other forms of administration, dependent upon the patient's condition, can be used.

It is noted that human subjects are treated generally longer than experimental animals, such that treatment has a length proportional to the length of the disease process and effectiveness. The doses may be single doses or multiple doses over a period of several days, weeks, months, years, or for the life of the recipient. Thus, one of skill in the art can routinely scale up from animal experiments, e.g., rats, mice, and the like, to humans, by techniques gleaned from this disclosure and documents cited herein and the knowledge in the art. The treatment generally has a length proportional to the length of the disease process and drug effectiveness and the subject being treated.

Examples of compositions comprising recombinant MAPCs include liquid preparations for administration, including suspensions; and, preparations for intramuscular or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, can be consulted to routinely prepare suitable preparations.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount, which will achieve the selected viscosity. Viscous compositions are normally prepared from solutions by the addition of such thickening agents.

A pharmaceutically acceptable preservative or cell stabilizer can be employed to increase the life of the compositions. Preferably, if preservatives are necessary, it is well within the purview of the skilled artisan to select compositions that will not affect the viability or efficacy of the MAPCs as described in the present invention.

Those skilled in the art will recognize that the components of the compositions should be selected to be chemically inert. This will present no problem to those skilled in chemical and pharmaceutical principles, or problems can be readily avoided by reference to standard texts or by routine experiments gleaned from the present disclosure and the documents cited herein.

The genetic defect corrected by methods of the invention can be at any known locus of a gene, whereby a functional gene product is not expressed. The preferred genes for various applications of the present invention encode FANCA, FANCB, FANCC, FANCD1, FANCD2, FANCE, FANCF, FANCG, hemoglobin, factor VIII, factor IX, erythropoietin, CFTR, collagen I, alpha 1 anti-trypsin, gamma-C, Rag1, Rag2, adenosine deaminase, phenylalanine hydroxylase, fumarate dehydroxylase, LDL receptor, aL-iduronidase or b-glucuronidase. More preferably, the gene encodes FANCC.

A specific example of the practical application of the patent invention is in treatment of Fanconi Anemia ("FA"). FA is an autosomal, recessive disorder. The clinical hallmark of FA is bone marrow failure. Such a deficiency in blood cell types is known to occur due to the progressive loss of hematopoietic progenitor cells (Fanconi, 1927). Congenital abnormalities and predisposition to several forms of cancer, such as acute myelogenous leukemia and squamous cell carcinoma also characterize patients suffering from this disease.

At present, the only mode of therapy to treat FA is blood marrow transplant. Recently, gene therapy efforts have been initiated by transfection of the intact gene into FA donor cells using viral vectors. However, there are several drawbacks to viral vectors that make them undesirable for therapeutic use. Methods of the present invention repair the defective gene in situ, yielding normal regulated gene expression and avoiding the random insertion events involved in other gene therapy methods.

Cells that are FANCC−/− can be selected by treatment of the cells with a dose of mitomycin C that is toxic to cells that do not express the gene product and non-toxic to cells that express the gene product. The preferred dose of mitomycin C is about 10 ng/ml for about 48 hours. Alternatively, FANCC−/− cells can be selected by treatment of the cells with a dose of cyclophosphamide and a dose of irradiation at levels that are toxic to cells that do not express the gene product and non-toxic to cells that express the gene product.

In one embodiment, the correction vector can comprise a gene encoding a selectable marker which confers a selectable phenotype, such as drug resistance, nutritional auxotrophy, resistance to a cytotoxic agent or expression of a surface protein. Selectable marker genes which can be used include, but are not limited to neo, gpt, dhfr, ada, pac, hyg, mdr1 and hisD. The selectable marker is preferably an antibiotic resistance gene. The selectable phenotype conferred makes it possible to identify and isolate MAPCs that have received the correction vector containing the selectable marker. Cells that integrate the construct will survive treatment with the selective agent. A subset of the stably transfected cells will be homologously recombined cells, which can be identified by a variety of techniques, including PCR, Southern hybridization and phenotypic screening.

The selectable marker can optionally be flanked at the 5' and 3' ends by lox P sites. In this embodiment, cells are selected based on expression of the selectable marker, and the selectable marker is excised by the Cre enzyme prior to transplantation. The Cre-lox P recombination system of bacteriophage P1 has been employed for genetic manipulation of higher eukaryotic cells (Sauer et al., 1988). Cre recombinase recognizes a 34 base pair Cre recombination signal sequence called lox P, and can delete genes which are flanked by two lox P sites in the same direction. Recombination of lox P sites can be achieved by transient transfection of a Cre expression plasmid (Araki et al., 1995) or by stable transfection of an inducible Cre recombinase construct. Alternatively, Cre can be introduced by crosslinking the polypeptide to the HIV trans-activating transduction (Tat) protein and introducing it into the cells. The Tat protein, when fused to a heterologous protein or peptide, can traverse biological membranes in a process called protein transduction (Mann et al., 1991; Anderson et al., 1993; Fawell et al., 1994).

Transformed MAPCs or their progeny are administered to the patient in need thereof, using known methods, via localized injection, including catheter administration, systemic injection, parenteral administration, including subcutaneous and intravascular, oral administration, central nervous system including intrathecal, intrahepatic, intrasplanchnic, intraperitoneal (including intraomental), renal subcapsular, or intramuscular or intrauterine injection into an embryo. Typically, a physician will determine the approximate cell dosage that will be most suitable for an individual subject. The specific dose for any particular subject may be varied and will depend upon a variety of factors including the age, body weight, general health, mode and time of administration and the severity of the particular condition in the subject undergoing transplantation.

Administration can be in conjunction with a pharmaceutically acceptable matrix, which may be biodegradable.

EXAMPLES

The following examples are provided as a further description of the invention, and to illustrate but not limit the invention.

Example 1

Isolation, Culture and Characterization of Mouse MAPCs

Mouse MAPCs (mMAPCs) were isolated, cultured and characterized essentially as described in Furcht et al. (PCT/US00/21387). All tissues were obtained according to guidelines from the University of Minnesota IACUC. Briefly, bone marrow mononuclear cells were obtained using Ficoll-Plaque density gradient centrifugation of bone marrow tissue from 5-6 week old ROSA26, C57/BL6, or FANCC−/− mice.

Alternatively, muscle and brain tissue was obtained from 3-129 day old ROSA26 or C57/BL6 mice. Muscles from the proximal parts of fore and hind limbs were excised and thoroughly minced. The tissue was treated with 0.2% collagenase (Sigma Chemical Co, St Louis, Mo.) for 1 hour at 37° C., followed by 0.1% trypsin (Invitrogen, Grand Island, N.Y.) for 45 minutes. Cells were then triturated vigorously and passed through a 70-um filter. Cell suspensions were collected and centrifuged for 10 minutes at 1600 rpm. Brain tissue was dissected and minced thoroughly. Cells were dissociated by incubation with 0.1% trypsin and 0.1% DNAse (Sigma) for 30 minutes at 37° C. Cells were then triturated vigorously and passed through a 70-um filter and centrifuged for 10 minutes at 1600 rpm.

Bone marrow mononuclear cells (BMMNC), or muscle or brain cell suspensions, were plated at a density of approximately $1 \times 10^5$ cells/cm² in expansion medium [2% fetal calf serum (FCS) in low glucose Dulbecco's minimal essential medium (LG-DMEM), 10 ng/mL each platelet derived growth factor (PDGF), epidermal growth factor (EGF) and leukemia inhibitory factor (LIF)] and maintained at a cell density of about $5 \times 10^3$ cells/cm². After 3-4 weeks, cells were recovered by trypsin/EDTA and were depleted of CD45$^+$/glycophorin (Gly)-A$^+$ cells with micromagnetic beads. The resulting CD45$^-$/Gly-A$^-$ cells were replated at 10 cells/well in 96-well plates coated with fibronectin (FN) and were expanded at cell densities between 0.5 and $1.5 \times 10^3$ cells/cm². The resulting mMAPCs had similar expansion potentials regardless of the tissue from which they were derived. Approximately 1% of wells seeded with 10 CD45$^-$/GlyA$^-$ cells yielded continuous growing cultures, suggesting that the cells capable of initiating MAPC cultures were rare. mMAPCs were approximately 8-10 μm in diameter with a large nucleus and scant cytoplasm. Several populations were cultured for more than 100 population doublings, and the morphology, phenotype and average telomere length of the cells remained unchanged throughout culture.

mMAPCs derived from bone marrow, muscle and brain were CD13$^+$, CD44$^-$, CD45$^-$, class-I and class-II histocompatibility antigen$^-$, Flk1$^{low}$ and cKit$^-$, as has previously been described for human MAPCs (Furcht et al., PCT/US00/21387). As with human cells, mMAPCs cultured on FN expressed transcripts for oct-4, and the LIF-R.

Example 2

Isolation, Culture and Characterization of Human MAPCs

Bone marrow tissue was obtained from healthy volunteer donors (age 2-50 years) after informed consent using guidelines from the University of Minnesota Committee on the use of Human Subject in Research. BMMNCs were obtained by Ficoll-Plaque density gradient centrifugation and depleted of CD45$^+$ and glycophorin-A$^+$ cells using micromagnetic beads (Miltenyii Biotec, Sunnyvale, Calif.).

Approximately $5 \times 10^3$ CD45$^-$/GlyA$^-$ cells were diluted in 200 μL expansion medium [58% DMEM-LG, 40% MCDB-201 (Sigma Chemical Co, St Louis, Mo.), supplemented with 1× insulin-transferrin-selenium (ITS), 1× linoleic-acid bovine serum albumin (LA-BSA), $10^{-8}$ M Dexamethasone, $10^{-4}$ M ascorbic acid 2-phosphate (all from Sigma), 100 U penicillin and 1,000 U streptomycin (Gibco) and 0-10% fetal calf serum (FCS) (Hyclone Laboratories, Logan, Utah) with 10 ng/ml of EGF (Sigma) and 10 ng/ml PDGF-BB (R&D Systems, Minneapolis, Minn.)] and plated in wells of 96 well plates that had been coated with 5 ng/ml of FN (Sigma). Medium was exchanged every 4-6 days. Once wells were >40-50% confluent, adherent cells were detached with 0.25% trypsin-EDTA (Sigma) and replated at 1:4 dilution in MAPC expansion medium and in bigger culture vessels coated with 5 ng/ml FN to maintain cell densities between 2 and $8 \times 10^3$ cells/cm².

Undifferentiated human MAPCs did not express CD31, CD34, CD36, CD44, CD45, CD62-E, CD62-L, CD62-P, HLA-class I and II, cKit, Tie, Tek, $\alpha_v\beta_3$, VE-cadherin, vascular cell adhesion molecule (VCAM), or intracellular adhesion molecule (ICAM)-1. MAPCs expressed low/very low levels of β2-microglobulin, $\alpha_v\beta_5$, CDw90, AC133, Flk1 and Flt1, and high levels of CD13 and CD49b.

Example 3

Differentiation of MAPCs into Multiple Cell Types

The differentiation ability of mouse, rat and human MAPCs was tested by adding differentiation factors (cytokines) that have previously been determined to be involved in the differentiation of ES cells into mesoderm, neuroectoderm, and endoderm. Differentiation required that cells were replated at 1-2×10$^4$ cells/cm$^2$ in serum free medium, without EGF, PDGF-BB and LIF, but with lineage specific cytokines. Differentiation was determined by RT-PCR, functional studies, and immunohistology for tissue specific markers. The tissue specific markers used were:
  (a) slow twitch myosin and MyoD for muscle,
  (b) von-Willebrand factor (vWF) and Tek for endothelium,
  (c) NF200 and MAP2 for neuroectoderm, and
  (d) cytokeratin-18 and albumin for endoderm The description below relates to differentiation of bone marrow-derived MAPCs. However, mMAPCs derived from muscle or brain were also tested, and could be induced to differentiate to mesoderm (endothelial cells), neuroectoderm (astrocytes and neurons) and endoderm (hepatocyte-like cells) using the same methods.

Neuronal Differentiation

Palmer et al. showed that neuroprogenitors can be cultured and expanded with PDGF-BB and induced to differentiate by removal of PDGF and addition of bFGF as a differentiation factor. Based on those studies and studies conducted using hMAPCs, mMAPCs were plated in FN coated wells without PDGF-BB and EGF but with 100 ng/mL bFGF. Progressive maturation of neuron-like cells was seen throughout culture. After 7 days, the majority of cells expressed nestin. After 14 days, 15-20% of MAPCs acquired morphologic and phenotypic characteristics of astrocytes (GFAP$^+$), 15-20% of oligodendrocytes (galactocerebroside (GalC)$^+$) and 50-60% of neurons (neurofilament-200 (NF-200)$^+$). NF200, GFAP or GalC were never found in the same cell, suggesting that it is unlikely that neuron-like cells were hMAPCs or glial cells that inappropriately expressed neuronal markers. Neuron-like cells also expressed Tau, MAP2 and NSE. Approximately 50% of neurons expressed gamma-amino-butyric-acid (GABA) and parvalbumin, 30% tyrosine hydroxylase and dopa-decarboxylase (DDC), and 20% serotonin and tryptophan hydroxylase. Differentiation was similar when MAPCs had been expanded for 40 or >90 population doublings. Quantitative RT-PCR, performed as described in WO 02/064748, confirmed expression of neuroectodermal markers: on day 2 MAPCs expressed otx1 and otx2 mRNA, and after 7 days nestin mRNA was detected.

The effect of fibroblast growth factor (FGF)-8b as a differentiation factor was tested next. This is important in vivo for midbrain development and used in vitro to induce dopaminergic and serotoninergic neurons from murine ES cells. When confluent human MAPCs (n=8) were cultured with 10 ng/mL FGF-8b+EGF, differentiation into cells staining positive for neuronal markers but not oligodendrocytes and astrocytes was seen. Cells had characteristics of GABAergic (GABA$^+$; 40±4%), dopaminergic (DOPA, TH, DCC and DTP$^+$, 26±5%) and serotoninergic (TrH, serotonin and serotonin-transporter$^+$, 34±6%) neurons. DOPA$^+$ neurons stained with antibodies against Nurr1, suggesting differentiation into midbrain DA neurons.

FGF-8b induced cells did not have the electrophysiological characteristics of mature neurons. Therefore, cells from 3-week old FGF-8b supported cultures were co-cultured with the glioblastoma cell line U-87, in the presence of FGF-8b, for an additional 2-3 weeks. Cells then acquired a more mature neuronal morphology, having increased cell size, cell number, and length and complexity of neurites. Furthermore, the cells acquired electrophysiological characteristics of mature neurons, i.e. a transient inward current, blocked reversibly by 1 µM tetrodotoxin (TTX), and having a time course and voltage-dependence typical of the type of voltage-activated sodium current found in mature neurons.

When human MAPCs (n=13) were cultured with 10 ng/ml brain-derived neurotrophic factor (BDNF)+EGF, differentiation was to exclusively DOPA, TH, DCC, DTP and Nurr1 positive neurons. Although BDNF supports neural differentiation from ES cells and neural stem cells (NSCs) (Peault, 1996; Choi et al. 1998), no studies have shown exclusive differentiation to DA-like neurons. Similar results were seen for mouse MAPCs induced with bFGF and for rat MAPCs induced with bFGF and BDNF.

Endothelial Differentiation

As an example of mesoderm, differentiation was induced to endothelium. Undifferentiated mouse MAPCs did not express the endothelial markers CD31, CD62E, Tek or vWF, but expressed low levels of Flk1. Mouse MAPCs were cultured in FN-coated wells with 10 ng/mL of the endothelial differentiation factor VEGF-B. Following treatment with VEGF for 14 days, >90% of MAPCs, irrespective of the number of population doublings they had undergone, expressed Flt1, CD31, vWF or CD62, consistent with endothelial differentiation. Like primary endothelial cells, MAPC-derived endothelial cells formed vascular tubes within 6 hours after replating in Matrigel™.

Similarly, human MAPCs express Flk1 and Flt1 but not CD34, Muc18 (P1H12), PECAM, E- and P-selectin, CD36, or Tie/Tek. When human MAPCs (2×10$^4$ cells/cm$^2$) were cultured in serum free medium with 20 ng/mL vascular endothelial growth factor (VEGF), cells expressed CD34, VE-cadherin, VCAM and Muc-18 from day 7 on. On day 14, they also expressed Tie, Tek, Flk1 and Flt1, PECAM, P-selectin and E-selectin, CD36, vWF, and connexin-40. Furthermore, cells could uptake low-density lipoproteins (LDL). Results from the histochemical staining were confirmed by Western blot. To induce vascular tube formation, MAPCs cultured for 14 days with VEGF were replated on Matrigel™ with 10 ng/mL VEGF-B for 6 hours. Endothelial differentiation was not seen when human MAPCs cultured in >2% FCS were used. In addition, when FCS was left in the media during differentiation, no endothelial cells were generated.

At least 1000-fold expansion was obtained when human MAPCs were sub-cultured, suggesting that endothelial precursors generated from human MAPCs continue to have significant proliferative potential. Cell expansion was even greater when FCS was added to the cultures after day 7.

When human MAPC-derived endothelial cells were administered intravenously (I.V.) in NOD-SCI mice that had a human colon-carcinoma implanted under the skin, contribution of the human endothelial cells could be seen to the neovascularization in the tumors. It may therefore be possible to incorporate genetically modified endothelial cells to derive a therapeutic benefit, i.e., to inhibit angiogenesis in cancer, or to promote angiogenesis to enhance vascularization in limbs or other organs such as the heart.

Endodermal Differentiation

Mouse MAPC differentiation into endoderm was tested. A number of different culture conditions were tested including culture with the differentiation factors keratinocyte growth factor (KGF), hepatocyte growth factor (HGF) and FGF-4, either on laminin, collagen, FN or Matrigel™ coated wells. When re-plated on Matrigel™ with 10 ng/mL FGF4 and 10 ng/mL HGF, approximately 70% of MAPCs acquired morphologic and phenotypic characteristics of hepatocyte-like cells. Cells became epithelioid, approximately 10% of cells became binucleated, and about 70% of cells stained positive for albumin, cytokeratin (CK)-18, and HNF-1P.

Endodermal-like cells generated in FGF4 and HGF containing cultures also had functional characteristics of hepatocytes, determined by measuring urea levels in supernatants of undifferentiated MAPCs and FGF4 and HGF-induced MAPCs using the Sigma Urea Nitrogen Kit 640 according to the manufacturer's recommendations. No urea was detected in undifferentiated MAPC cultures. Urea production was 10 µg/cell/hr 14 days after adding FGF4 and HGF and remained detectable at similar levels until day 25. This is comparable to primary rat hepatocytes grown in monolayer. Presence of albumin together with urea production supports the notion of hepatic differentiation from MAPCs in vitro.

Given the likely existence of an endodermal lineage precursor cell, MAPC likely give rise to a cell that forms various cells in the liver in the pancreas both exocrine and endocrine components and other endodermal derived cell tissue lineages.

Hematopoietic Differentiation

The ability of MAPCs to differentiate into hematopoietic cells was tested. eGFP transduced human MAPCs that were GlyA, CD45 and CD34 negative (n=20), were co-cultured with the mouse yolk sac mesodermal cell line, YSM5, as suspension cell aggregates for 6 days in serum free medium supplemented with 10 ng/mL bFGF and VEGF. After six days, only eGFP$^+$ cells (i.e., MAPC progeny) remained and YSM5 cells had died.

Remaining cells were transferred to methylcellulose cultures containing 10% fetal calf serum supplemented with 10 ng/mL bone morphogenic protein-4 (BMP4), VEGF, bFGF, stem cell factor (SCF), Flt3L, hyper IL6, thrombopoietin (TPO), and erythropoietin (EPO) for 2 weeks. In these cultures, both adherent eGFP$^+$ cells and small, round non-adherent cells, which formed many colonies attached to the adherent cells, were detected. The non-adherent and adherent fractions were collected separately and cultured in 10% FCS containing medium with 10 ng/mL VEGF and bFGF for 7 days. Adherent cells stained positive for vWF, formed vascular tubes when plated on ECM, and were able to uptake a-LDL, indicating their endothelial nature. 5-50% of the non-adherent cells stained positive for human specific GlyA and HLA-class I by flow cytometry. Gly-A$^+$/HLA-class-I$^+$ cells were selected by FACS. On Wright-Giemsa, these cells exhibited the characteristic morphology and staining pattern of primitive erythroblasts. Cells were benzidine and human hemoglobin (Hb) positive. By RT-PCR it was determined that these cells expressed human specific Hb-e, but not Hb-a.

When replated in methylcellulose assay with 20% FCS and EPO, small erythroid colonies were seen after 10 days, and 100% of these colonies stained positive for human specific GlyA and Hb. As selection of MAPCs depends on the depletion of CD45$^+$ and Gly A$^+$ cells from bone marrow, and cultured MAPCs were CD45$^-$ and GlyA$^-$ at all times examined, using both FACS and cDNA array analysis, it is very unlikely that these results were due to contamination of MAPCs with hematopoietic cells.

Example 4

Homing and Engraftment of Mammalian MAPCs into Numerous Organs in the Body mMAPCs were tested to determine whether they had the ability to engraft and differentiate in vivo into tissue specific cells. mMAPCs were grown as described in Example 1 from a LacZ transgenic C57 Black 6, ROSA 26 mouse. $10^6$ mMAPCs from the LacZ mouse were injected intravenously into NOD-SCID mice tail veins, with or without 250 Rads of total body radiation 4-6 hrs prior to the injection. The animals were sacrificed by cervical dislocation at 4-24 weeks after the injections.

Tissue Harvest

Blood and Bone Marrow:

0.5-1 ml of blood was obtained at the time animals were sacrificed. Bone marrow was collected by flushing femurs and tibias. For phenotyping, red cells in blood and bone marrow were depleted using ice cold ammonium chloride (Stem Cell Technologies Inc., Vancouver, Canada) and $10^5$ cells were used for cytospin centrifugation. For serial transplantation, $5 \times 10^7$ cells from 2 femurs and 2 tibias were transplanted into individual secondary recipients via tail vein injection. Secondary recipients were sacrificed after 7-10 weeks.

Solid Organs:

Lungs were inflated with 1 ml 1:4 dilution of OCT compound (Sakura-Finetek Inc, USA) in PBS. Specimens of spleen, liver, lung, intestine, skeletal muscle, myocardium, kidney and brain of the recipient animals were harvested and cryopreserved in OCT at –80° C. and in RNA Later (Ambion Inc., Austin, Tex., USA) at –20° C. for quantitative PCR.

mMAPCs Engraft and Differentiate Into Tissue Specific Cells In Vivo

Engraftment of the β-gal/neomycin (NEO) transgene-containing cells (Zambrowicz et al., 1997) was tested by immunohistochemistry for β-gal and by quantitative-PCR for the NEO gene. Immunohistochemistry as described in WO 02/064748.

Engraftment, defined as detection of >1% β-gal positive cells, was seen in hematopoietic tissues (blood, bone marrow and spleen) as well as epithelium of lung, liver, and intestine of all recipient animals tested as shown in Table 1 below.

TABLE 1

| | Time | Engraftment levels (%) determined by immunofluorescence or (quantitative -PCR) | | | | | | |
|---|---|---|---|---|---|---|---|---|
| Animal | (Weeks) | Radiation | Marrow | Blood | Spleen | Liver | Lung | Intestine |
| 1 | 4 | No | 2 (1) | 2 | 5 | 7 | 4 | 2 |
| 2 | 5 | No | 3 (4) | 4 | 5 | 9 | 5 | 3 |
| 3 | 10 | No | 1 | 3 | 3 | 6 | 3 | 2 |
| 4 | 16 | No | 4 | 2 | 3 | 4 | 3 | 4 (4.9) |
| 5 | 24 | No | 3 | 2 | 3 | 6 | 4 | 1 |
| 6 | 8 | Yes | 8 (8) | 6 | 4 | 5 | 2 (1.1) | 7 |
| 7 | 8 | Yes | 10 | 8 | 7 (7.3) | 4 | 6 | 8 |
| 8 | 8 | Yes | 5 | 8 | 3 | 5 | 5 | 6 |

TABLE 1-continued

| | | | Engraftment levels (%) determined by immunofluorescence or (quantitative -PCR) | | | | | |
|---|---|---|---|---|---|---|---|---|
| Animal | Time (Weeks) | Radiation | Marrow | Blood | Spleen | Liver | Lung | Intestine |
| 9 | 8 | Yes | 7 | 5 | 5 | 6 | 4 | 6 |
| 10 | 10 | Yes | 5 (6) | 7 | 9 (12.5) | 5 | 2 | 8 |
| 11 | 11 | Yes | 8 | 8 | 6 | 5 | 3 | 10 (11.9) |
| 12 | 11 | Yes | 6 | 5 | 4 | 8 (6.2) | 10 (12.3) | 8 |
| SR-1 | 7 | Yes | 6 | 7 | 5 | 1 (1.7) | 5 | 8 |
| SR-2 | 10 | Yes | 5 | 4 | 8 | 3 | 4 | 6 |

These results show that mammalian MAPCs can be purified, expanded ex vivo, infused I.V., and can home to various sites in the body, engraft into numerous organs, and that the cells are alive in these various organs one month or longer. Such donor cells, and undifferentiated and differentiated progeny of them, are found in organs including, but not limited to, bone marrow, spleen, liver and lung. MAPCs can thus be used to repopulate one or more compartment(s), or to augment or restore cell or organ function.

Example 5

MAPCs Can be Effectively Transfected

In order for MAPCs to be successfully used in gene targeting/gene correction applications, the cells must be amenable to transfection. Several experiments were performed to determine a) whether MAPCs can be transfected and b) if so, which transfection methods are most effective. All transfections were performed using a mammalian green fluorescent protein (GFP) expression vector pEGFP-N1 (Clontech). In each case, 10 ug of DNA was transfected into $0.3 \times 10^6$ cells. Expression of GFP was determined 2 days after transfection by visualizing cells using a fluorescence microscope (excitation wavelength of approximately 488 nm) and counting the % of cells displaying green flourescence. The transfection methods used were:
  (a) Calcium phosphate precipitation (CalPhos kit; Clontech);
  (b) Effectene™ (Qiagen): according to manufacturer's instructions;
  (c) DMRIE-C (Invitrogen): according to manufacturer's instructions;
  (d) AVET (Bender Med Systems);
  (e) AVET+DMRIE-C: preincubation of the AVET-DNA complex with the DMRIE-C transfection reagent for 30 minutes at 37° C. followed by overnight incubation with cells to be transfected;
  (f) Superfect™ (Gibco-BRL): according to manufacturer's instructions;
  (g) electroporation; and
  (h) nucleoporation.

Most of the known methods of transfection tested were found to be sub-optimal in MAPCs, owing to the requirement that they must be grown at a low cell density of about 500 cells/cm² in order to remain undifferentiated. Of the transfection methods that were tried, Superfect, a liposome mediated method, electroporation, and nucleoporation gave the best results, having a significant number of transfectants (FIG. 1). The optimized nucleoporation method described herein was the preferred method, yielding a significant percentage of stable transfectants at cell densities low enough to maintain MAPCs in an undifferentiated state.

For transfection with Superfect, MAPCs were seeded at high density, and a transfection rate of 15-18% was achieved at 24 hours post transfection. This mode of transfection requires the cells to be at high density, which is not optimal for MAPCs since close cell-cell contact leads to differentiation of the cells and loss of stem cell-like properties.

Figure 2:
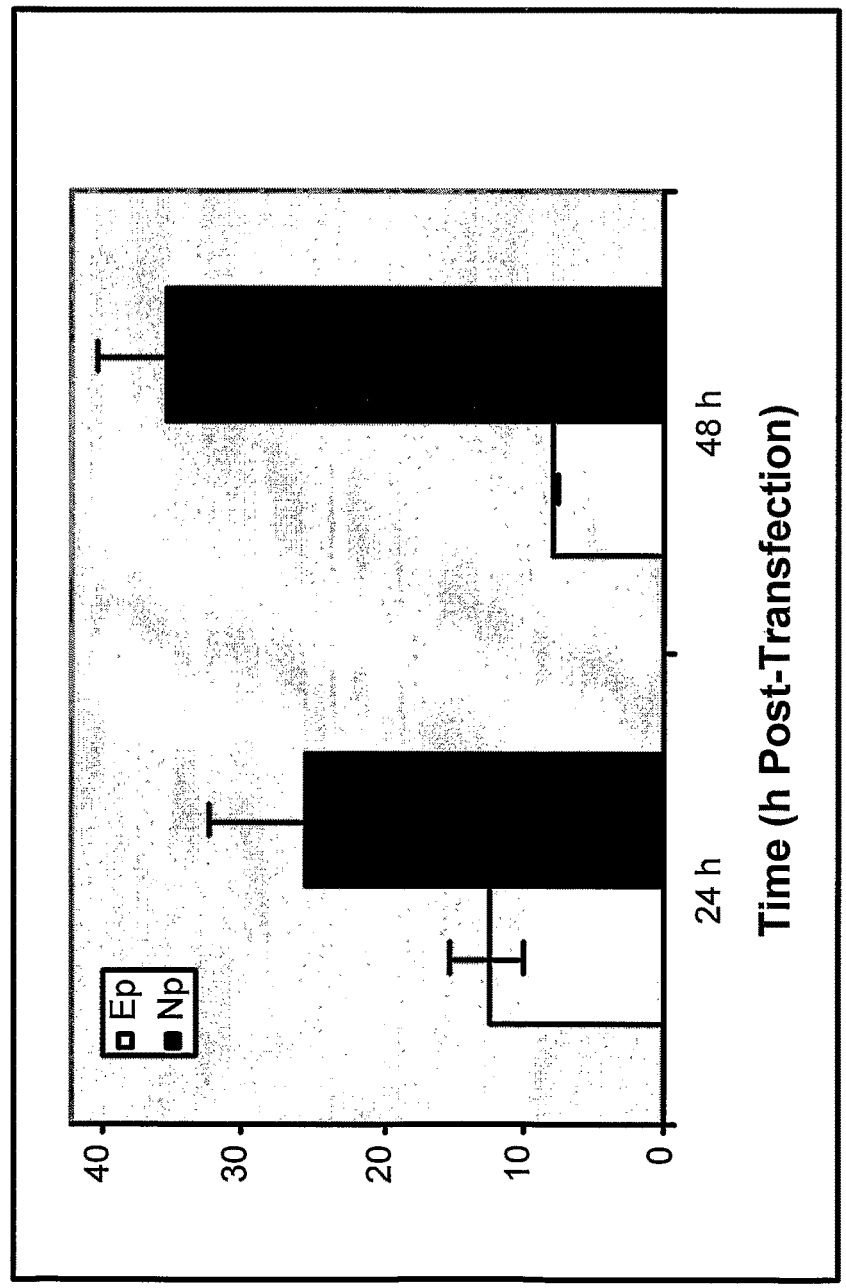
FIG. 2 shows the percentage of cells expressing GFP at 24 and 48 hours after transfection by electroporation (Ep) or nucleoporation (Np).

After transfection using electroporation at 330V, about 12-15% MAPCs were positive at 24 hours post transfection (FIGS. 1 and 2). However, the number of transfected cells decreased to about 5-8% by 48 hours post transfection (FIG. 2), and stable transfectants were not observed over a period of 3 weeks in culture.

Nucleoporation, a method of electroporation that uses a combination of special transfection solutions with electric parameters was then performed. A sample of about 200,000 cells or greater was trypsinized and spun down. Media was removed (residual media removed by pipette). It is important to remove all media since volumes can change when excess media is left behind. Nucleofection solution (100 ul) from Amaxa Inc. was added (the Amaxa Kit used for human MSCs is preferred, but comparable results can be obtained with mES kit and Kit V). Cells were pipetted up and down gently to form a uniform suspension. DNA was added up to a maximum concentration of 60 ug DNA per ml. The suspension was mixed and transferred to a 4 mm electrode gap cuvette (supplied by Amaxa Inc.) without introducing air bubbles. The cuvette was placed in the cuvette holder, and the nucleoporator was set to Program A-23 (also supplied by Amaxa Inc.).

After nucleoporation, the cuvette was removed from the holder. The cells were retrieved using plastic pipettes and transferred to eppendorf tubes containing 1 ml MAPC media pre-warmed to 37° C. The cells were stabilized at 37° C. for 5-10 minutes. The transfected MAPCs were then spun down using a desktop centrifuge and plated on FN-coated plates. Alternatively, cells can be plated directly onto FN-coated plates without centrifugation. Assuming 75% cell death, cells were plated at appropriate density. Media was replaced after 12-16 hours and cells were monitored for gene expression.

While different nucleofection solutions (Amaxa Inc.) showed a minor variation in the transfection efficiency, the Program A-23 yield was as high as 25% transfection in mouse MAPCs at 24 h post transfection, and nearly 35% at 48 h post transfection (FIG. 2). This result was much higher than the efficiencies obtained with Superfect or electroporation. Further, stable cells that were resistant to the drug hygromycin were generated following transfection with a plasmid carrying this resistance gene. This indicates that the program and nucleoporation solution were not toxic to MAPCs. Similar results were obtained with human MAPCs (10-14% transfection efficiency) and rat MAPCs (over 30% transfection efficiency).

With this approach, MAPCs only need to be kept at high density transiently, during a course of nucleoporation that does not exceed 5 minutes. Therefore, the cells are not exposed to high cell density conditions for a long period, and hence can be maintained in an undifferentiated state.

Example 6

Gene Targeting Can be Effectively Achieved in MAPCs

In order to test whether MAPCs are susceptible to gene targeting by homolgous recombination, the hypoxanthine phosphoribosyl transferase (HPRT) gene was targeted. HPRT catalyzes the synthesis of inosinate, a precursor of AMP and GMP. Cells expressing functional HPRT can grow in media containing hypoxanthine, aminopterin and thymidine (HAT media). Conversely, cells expressing functional HPRT are sensitive to media containing 6-thioguanine (6-TG) and cannot grow in it.

Figure 3:
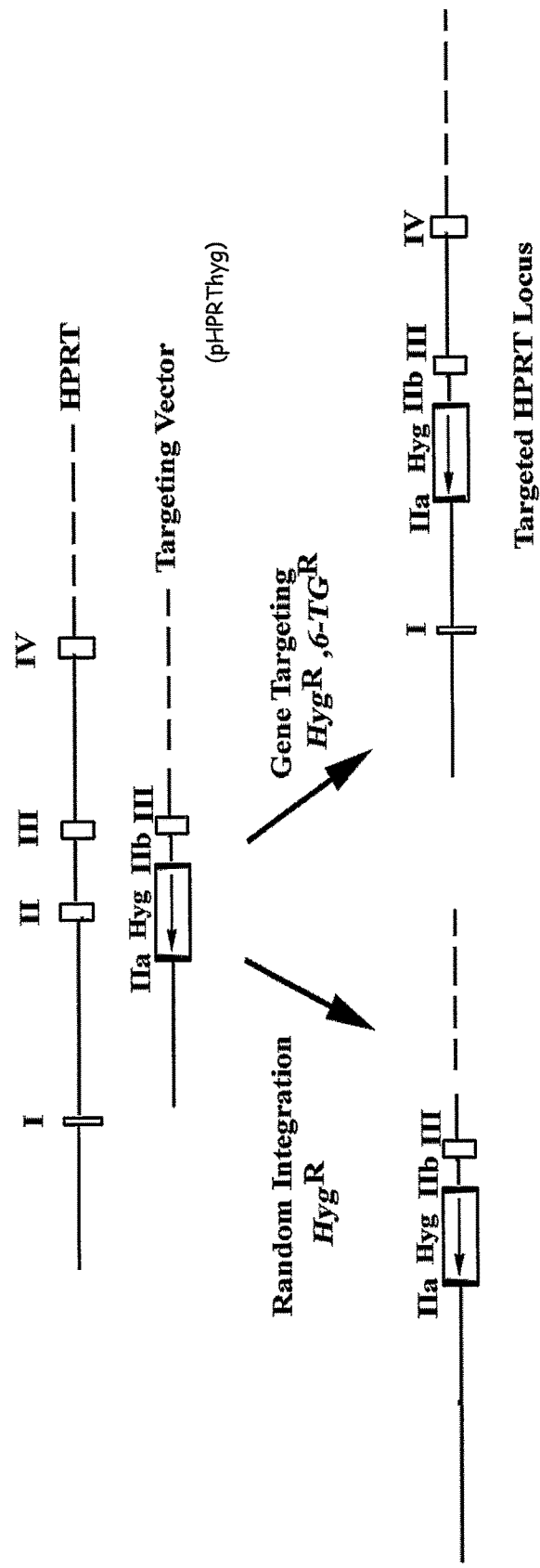
FIG. 3 shows the HPRT gene and the vector used to target it in MAPCs.

The HPRT locus was targeted using the vector illustrated in FIG. 3. This vector contains sequence from exons II and III of the HPRT gene, but has a hygromycin resistance ($Hyg^R$) gene inserted within the exon II sequence. Thus, successful homologous recombination of the targeting vector with the wild type HPRT gene results in expression of a truncated, non-functional HPRT gene product, and cells become 6-TG resistant ($6-HT^R$). In some cells random integration of the targeting vector may occur. However, these cells can be readily distinguished from those cells in which correct targeting of the HPRT locus has been achieved, as only those cells where the HPRT locus has been disrupted (i.e. by homologous recombination of the targeting vector) will be 6-TG resistant. All cells containing the vector will be hygromycin resistant, regardless of where in the genome it is integrated.

MAPCs were grown in HAT media for 3-5 days, seeded, and cultured for 12-16 hours as described in Example 2. The current protocols in the art for gene targeting needed to be modified to accommodate MAPCs. MAPCs were maintained at low density during all steps of the procedure, including during drug selection (where corrected cells are generally picked as colonies). In contrast to other protocols known in the art, MAPCs were seeded in 96 well plates, and targeted clones were picked and maintained at low density.

The cells were transfected with the HPRT targeting vector pHPRThyg (provided by Andrew Porter, MRC, London; Yanez and Porter ACG (1999) Gene Therapy 6:1282-1290), linearized with the restriction endonuclease Sal I, using Superfect™ according to the manufacturer's instructions (3 hour treatment). Cells were then trypsinized, seeded at normal MAPC plating density, and grown for 2 days. Cells were grown for three more days in the presence of 120 mg/ml hygromycin to select successfully transfected cells. Fresh media containing hygromycin (120 mg/ml) and 6-HT (15 mg/ml) was added to the cells and they were cultured for 7 days.

Figure 4:
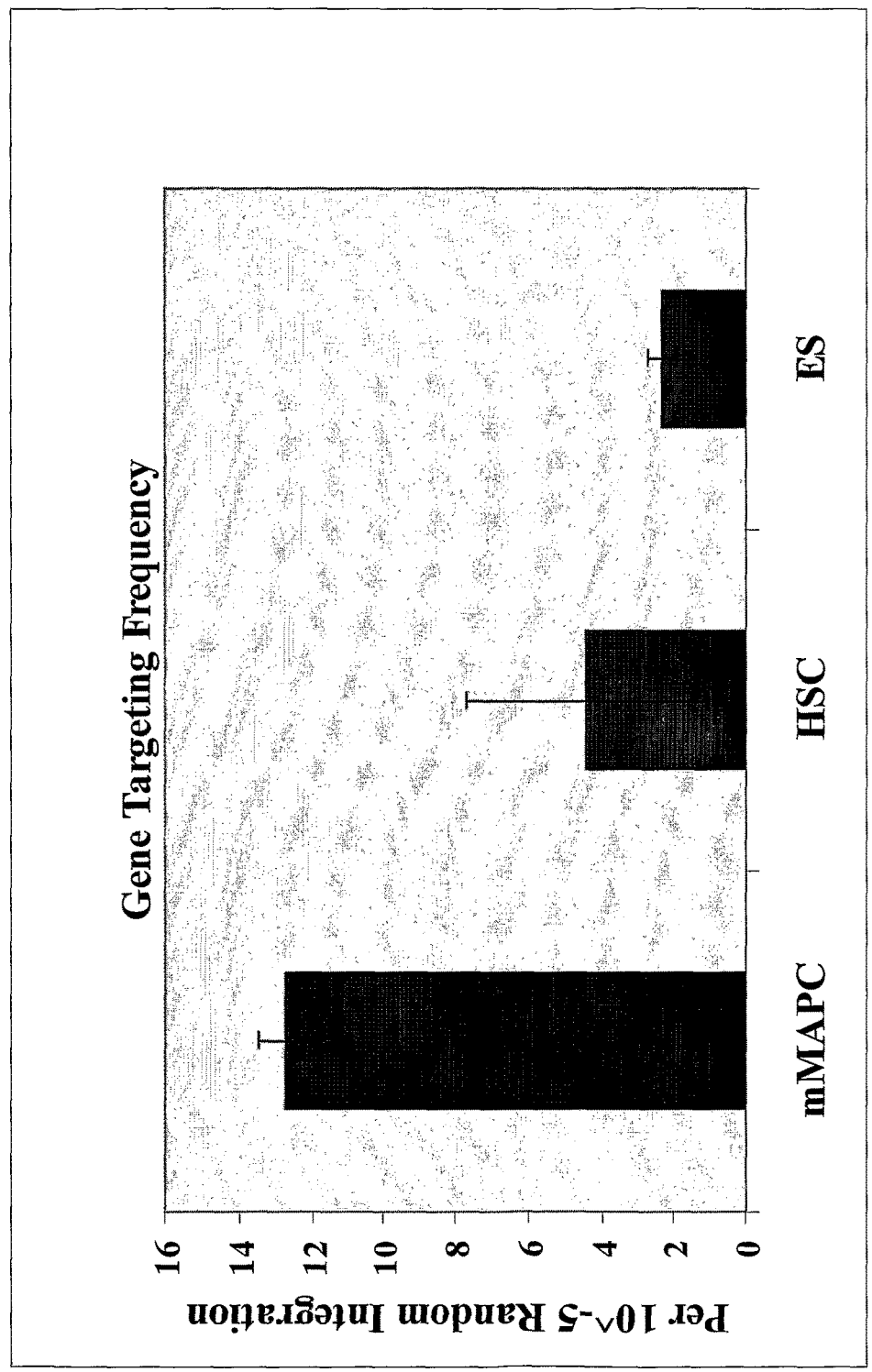
FIG. 4 shows the gene targeting frequency in mMAPCs compared with the frequency in HSC and ES cells (Hatada et al., 2001).

This targeting experiment was repeated on two separate occasions. The results are illustrated in Table 2 and in FIG. 4, and show that MAPCs can be successfully targeted at the HPRT locus. Furthermore, the results shown in FIG. 4 illustrate that the level of targeting that can be achieved using MAPCs is even higher than that described previously by Hatada at el. (2001) for ES cells and HSCs.

TABLE 2

| | Number of $Hyg^R$ cells | Number of $6TG^R$ cells | Gene Targeting Frequency ($\times 10^{-5}$) |
|---|---|---|---|
| Experiment 1 | 44,000 | 5 | 12 |
| Experiment 2 | 37,000 | 5 | 13.5 |

Example 7

Gene Correction and Phenotype Reversal in Mouse Model of Fanconi Anemia

Fanconi Anemia (FA) is an autosomal, recessive disorder resulting in congenital abnormalities, bone marrow failure and predisposition to several forms of cancer. At present the only mode of therapy to treat FA is bone marrow transplant. Recently, gene therapy efforts have been initiated involving transfection of the intact gene in to FA donor cells using viral vectors. However, such methods are plagued by random insertion events. An ideal solution would be to repair the defective gene itself, thereby yielding naturally regulated FA protein expression. The methods of the present invention can be used to deliver to animals genetically corrected MAPCs that produce clinically relevant levels of FA protein, and can thus be used in the treatment for FA.

Mice with disrupted FA genes have been created. For example, Whitney et al. (1996 generated a mouse in which expression of the FA complementation group C gene (FANCC) was disrupted. This FANCC-/- "knock out" mouse has a neomycin cassette replacing exon 9 of the gene, which results in a frame-shift that leads to the formation of a truncated, non-functional FANCC protein. These mice display many of the characteristics of human FA, for example hypogonadism and reduced fertility and development of pancytopenia (resulting from marrow aplasia) upon exposure to mitomycin C.

Figure 5:
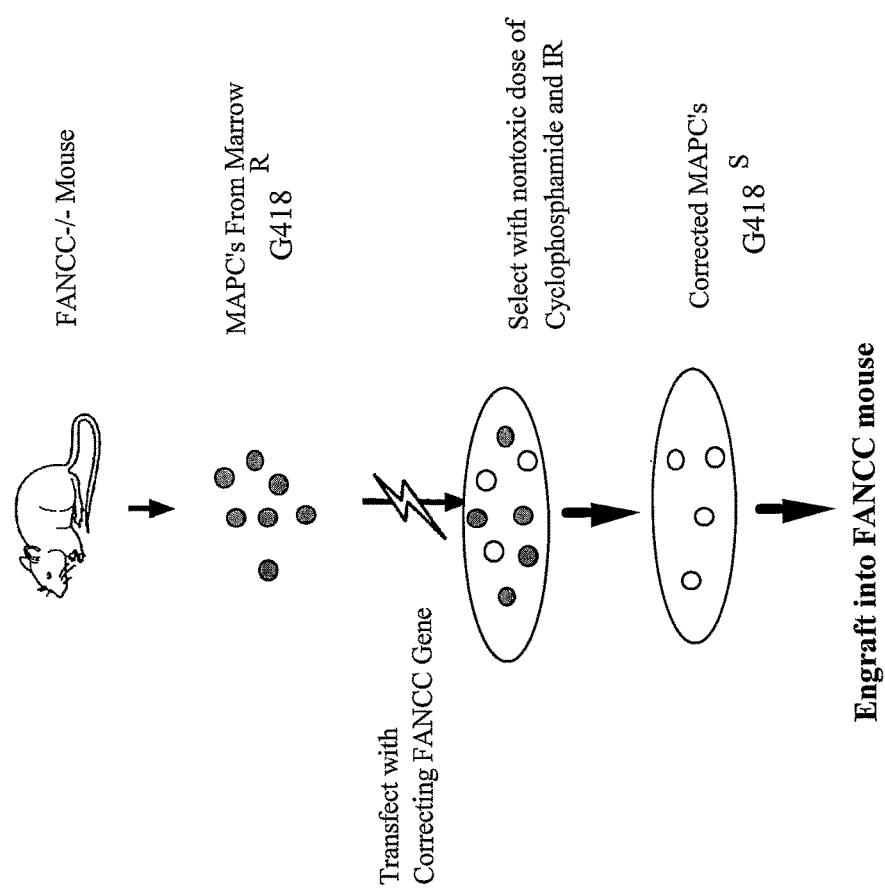
FIG. 5 provides an overview of the experimental strategy for gene repair in a knockout mouse model system.

The methods of the present invention can be used to correct the genetic and phenotypic defects in the above FANCC-/- knockout mice, as illustrated in FIG. 5, and as described in this example.

Isolation of MAPCs from the FANCC-/- Mouse.

MAPCs are generally isolated from bone marrow cells. Because the bone marrow of some Fanconi patients may be defective, MAPCs are particularly well-suited for use in these patients because they can be isolated from tissues other than bone marrow. In the case of FANCC-/- mice, muscle and heart cells were also used to generate MAPCs. Brain can also be used for isolation of MAPCs, as is discussed in Example 1. Isolated cells were plated in MAPC expansion medium, consisting of DMEM-LG (58%, Gibco-BRL. Grand Island, N.Y.), MCDB-201 (40%, Sigma Chemicals Co, St Louis, Mo.), 2% FCS (Hyclone Laboratories, Logan, Utah) supplemented with 1× insulin-transferrin-selenium (ITS), 1× linoleic acid-bovine serum albumin (LA-BSA), $10^{-8}$ M dexamethasone, $10^{-4}$ M ascorbic acid 2-phosphate (AA), 100 U penicillin and 1,000 U streptomycin, in wells of a 6 well plate. Following expansion of cells in culture for about 2-3 weeks, cells were sub cloned at 5 or 10 cells per well in a 96 well plate and growing colonies were chosen and expanded. Four different clones were chosen for the study, of which one of the clones that was 90% diploid and cytogenetically normal was chosen for further characterization.

The morphology of the FANCC-/- cells is spindle shaped, with an average size of 11 μm. Normal mouse MAPCs are also spindle shaped, with a size of 10-15 µm. Further, the phenotype of FANCC−/− cells is remarkably similar to that of mouse MAPCs (Table 3).

TABLE 3

| Markers | MAPC Phenotype | FANCC −/− Bulk n = 4 | C#HB2 n = 14 |
| --- | --- | --- | --- |
| CD45 | Negative | Negative | Negative |
| CD31 | N.A. | <1% Positive | Negative |
| CD34 | Negative | Negative | Negative |
| CD44 | Negative | Negative | Negative |
| Sca-1 | Positive - dim | ~50% Positive | ~90% Positive |
| Gr-1 | N.A. | Negative | Negative |
| Thy-1 | Negative | ~50% Positive | <10% Positive |
| Flk-1 | Negative | Negative | Negative |
| cKit | N.A. | Negative | Negative |

Figure 6:
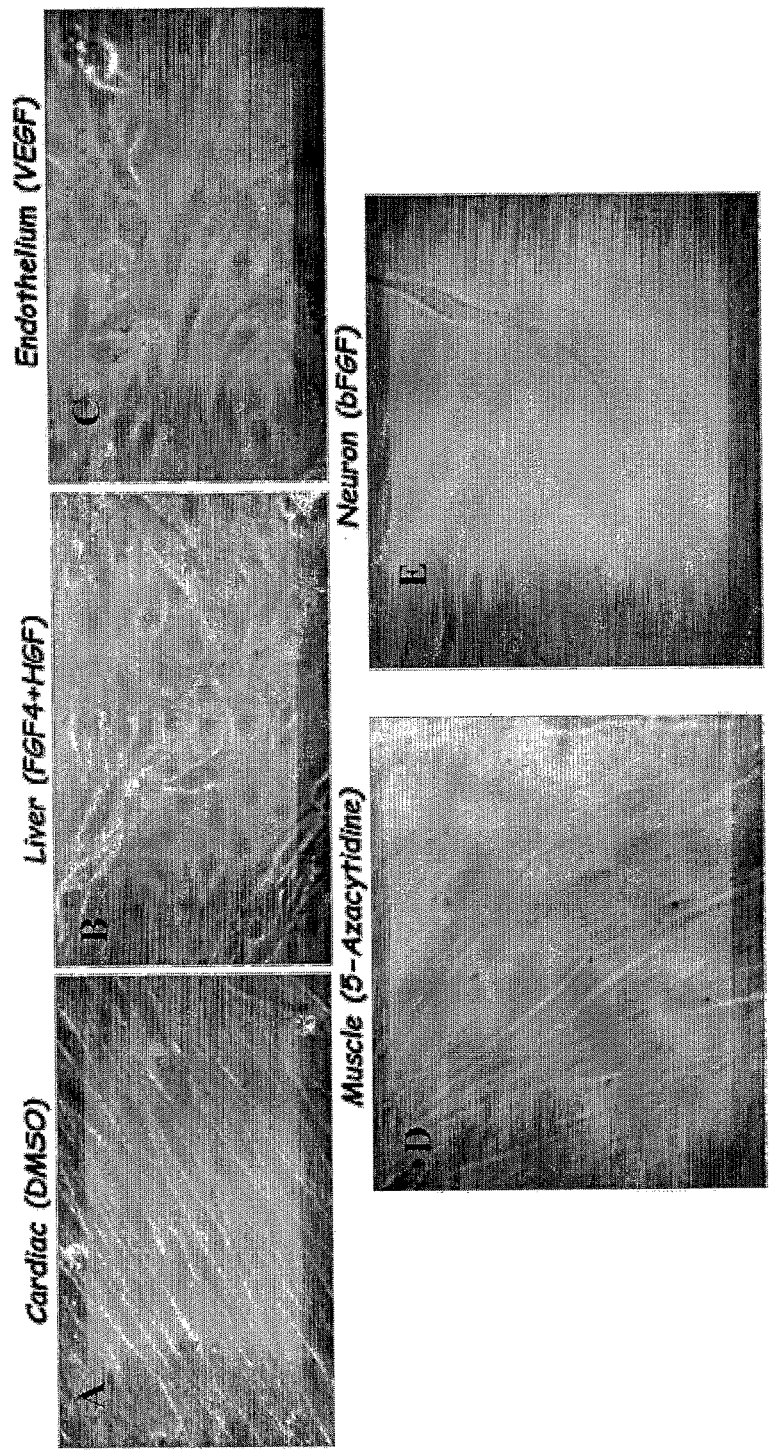
FIG. 6 shows FANCC−/− MAPCs that have differentiated into cardiac cells (6A), liver cells (6B), endothelial cells (6C), muscle cells (6D) and neurons (6E).

In order to demonstrate that the FANCC−/− cells are indeed multipotent, cells were seeded for differentiation into multiple lineages. FIG. 6 shows morphological changes of FANCC−/− cells following exposure to appropriate cytokines, as described in Example 3, for 11 days in culture.
Correction of the FANCC Gene by Homologous Recombination.

Figure 7:
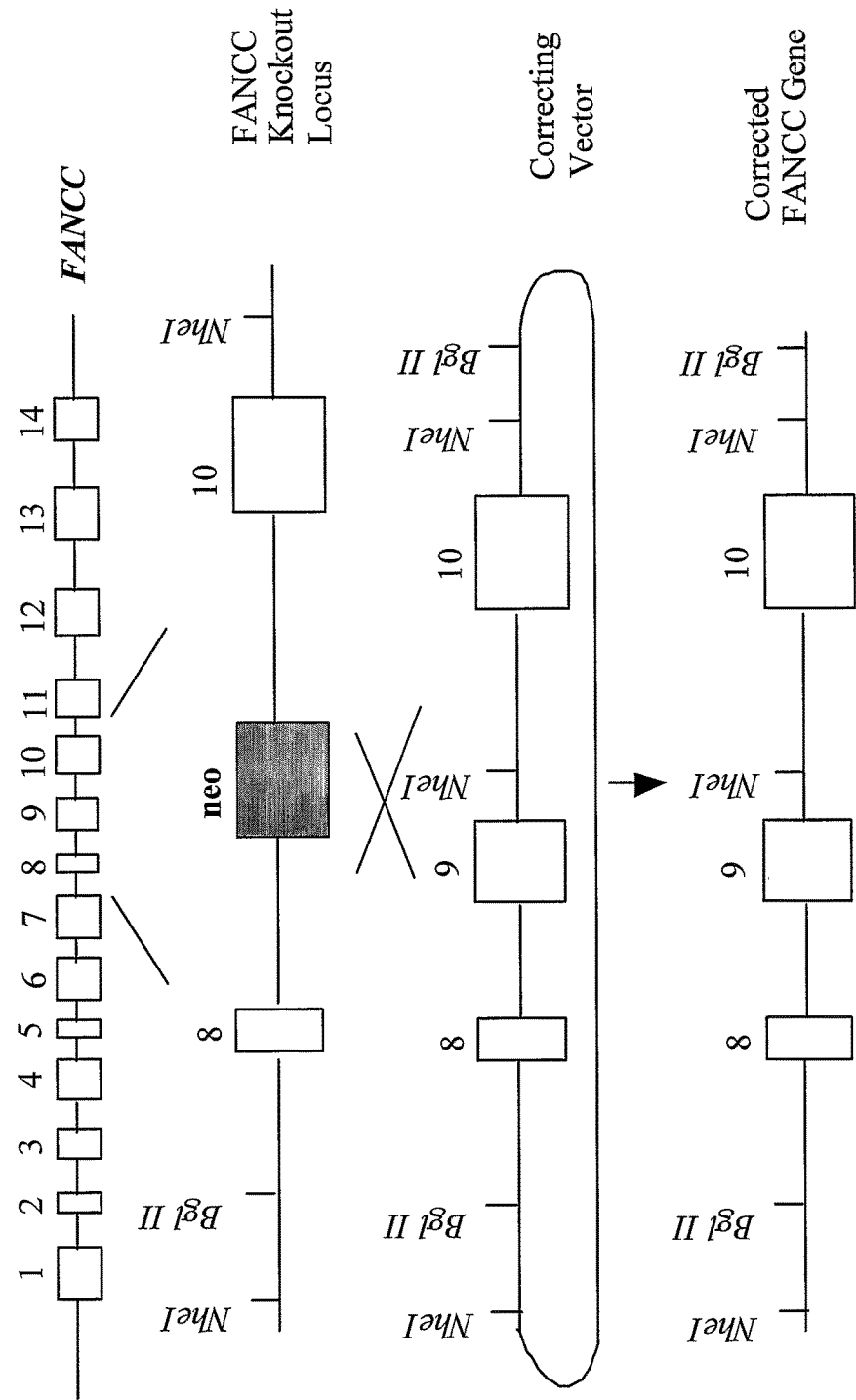
FIG. 7 shows schematic diagrams of the FANCC gene, containing 14 exons, the knockout locus in Fanconi anemia model mice, and the correction vector used to correct the defective FANCC gene.

Once MAPCs have been isolated as described above, a correction vector can be used to replace the defective segment of the gene by homologous recombination. This correction vector (FIG. 7) can be made as follows: Vector p7A, described by Whitney et al. (1996) comprises a 13.4 kb BglII/NheI fragment derived from a lambda clone and spanning exons 8, 9, and 10 of the mouse FANCC gene, cloned into the commercially available pBluescript® cloning vector (Stratagene Inc.). A fragment spanning the disrupted region of the mouse FANCC gene in the FANCC−/− knockout, is excised from p7A and sublconed into any suitable mammalian vector that has an appropriate drug resistance marker. In the present example, the AgeI/ApaBI sites (within the BglII/NheI fragment) are used to sublcone approximately 10217 by of sequence spanning exons 8 and 9 of the mouse FANCC gene, into the mammalian expression pREP4, which has hyg resistance marker, to generate the final correction vector. The AgeI/ApaBI fragment in the correction vector has 4266 bp of sequence upstream of the 2498 bp disruption in the FANCC−/− knockout, and 3403 bp of downstream sequence, thus providing sufficient homology to promote gene targeting by homolgous recombination. The total length of the correction vector is 10217 bp.

Mouse FANCC−/− MAPCs are transfected with the correction vector by the methods described in Example 5. Alternatively, MAPCs may be transfected immediately after bone marrow harvesting. In those cells where homologous recombination spontaneously occurs, the neo selection cassette is replaced with the natural exon 9 sequence from the mouse FANCC gene. Thus, corrected cells are not neomycin resistant and cannot grow in media containing neomycin or G418. Corrected cells are selected by exposing the MAPCs to 10 ng/ml mitomycin C for about 48 hours.
Characterization of the Corrected Cells.

The correction of the FANCC gene is confirmed using RT-PCR analysis. The predominant cellular phenotype of FA is chromosomal instability and hypersensitivity to DNA cross linking agents such as mitomycin C and cyclophosphamide (Sasaki & Tonomura, 1973; Auerbach & Wolman, 1976; Ishida & Buchwald, 1982). Therefore, a reduction in sensitivity to mitomycin C and/or cyclophosphamide, and a reduction in chromosomal instability, are used as measure of phenotypic correction of MAPCs.

(a) RT PCR Analysis.

Total cytoplasmic RNA is isolated from FANCC−/−, corrected and wild type MAPCs. Reverse transcription with random hexamer primers is performed to generate a cDNA copy of the mRNA, using standard procedures known in the art. This cDNA is then used as the template in PCR reactions. The forward primer has sequence from exon 8 of the FANCC gene (5'-CTGCCAACCTGCCATCTTCAG-3') (SEQ ID NO:3) and the reverse primers have sequences from exon 9 (5'-AAGAGCAGCTAGTACTTCTGG-3') (SEQ ID NO:4) or exon 10 (5'-AGGAAAGTAGGTCCT-GAGGG-3')(SEQ ID NO:5). PCR products are radioactively labeled by incorporation of $^{32}P$ dATP into the PCR reaction mixture. PCR products are separated on a 5% polyacrylamide gel and the gel is exposed to a phosphorimager screen overnight. Confirmation of the correction of the FANCC gene is obtained by comparison of the PCR product bands in the presumed corrected and wild type MAPCs. The major PCR product in MAPCs that have been corrected is the same size as that found in wild-type MAPCs, but differs in size from that found in uncorrected FANCC−/− MAPCs.

(b) Cell Cycle Analysis

FA cells are known to arrest at the G2 phase of the cell cycle following treatment with mitomycin C (Heinrich et al., 1998), therefore functional correction of the FANCC−/− phenotype can be tested by determining if mitomycin C causes G2 arrest. FANCC−/−, corrected and wild type MAPCs, are treated with 10 ng/ml mitomycin C for 48 hours. Approximately $1 \times 10^6$ MAPCs are then fixed in 70% ethanol overnight, digested with RNase A, and stained with propidium iodide according to standard procedures. Following staining, the samples are analyzed for DNA content by flow cytometry using Cell Quest Pro on a FACSCalibur flow cytometry machine, with an excitation wavelength of 488 nm and an emission wavelength of 585 nm. The histogram data generated is analyzed using Modfit software (Verity Software House, Top sham, ME), to determine the cell cycle distribution. By comparing the cell cycle distributions of the presumed corrected cells with those of wild type and FANCC−/− MAPCs, it can readily be determined whether reversal of mitomycin C sensitivity has occurred.

(c) Chromosome Breakage Analysis.

FA cells are known to exhibit increased chromosomal breakage and radial formation (Auerbach & Wolman, 1976; Auerbach, 1993). FANCC−/− corrected and wild type MAPCs are exposed to various concentrations of clastogens for 24 hours, then treated with colcemid for 3 hours and placed in a hypotonic medium consisting of 25% fetal calf serum and $dH_2O$, and fixed to slides. Following staining with Wright's stain, chromosomes are scored for breaks and radials per cell. A level of chromosome breaks and radials similar to that found in wild type MAPCs is indicative of correction of the FANCC−/− phenotype.
Transplantation of the Corrected Cells into FANCC−/− Mice The corrected MAPCs are transplanted into FANCC−/− mice by tail vein injection according to established procedures. Approximately, $1 \times 10^6$ undifferentiated corrected MAPC's are injected into non-irradiated and irradiated 6-9 week old FANCC−/− knockout mice. To confirm the presence of corrected gene, PCR analysis of peripheral blood is carried out 4-6 weeks after transplantation, using primers specific for the corrected gene. The corrected cells are selected in vivo using two mitomycin C dosing regimes: a) an acute dose of 1 mg/kg/week and b) a chronic dose of 0.3 mg/kg/week.

Reversal of the Phenotype Associated with FANCC Deficiency

After the presence of corrected gene is confirmed, 0.3 mg/kg mitomycin C (Calbiochem, La Jolla, Calif.) is administered to the mice, via intraperitoneal injection, daily for 2-3 weeks. Such administration of mitomycin C is known to cause pancytopenia and bone marrow aplasia in FANCC−/− mice (Carreau et al., 1998). By comparing peripheral blood cell counts between the presumed corrected, FANCC−/− and wild type mice at various time points, reversal of the FANCC−/− phenotype can be confirmed.

Example 8

Correction of Fanconi Anemia in Humans

Human Fanconi Anemia (FA) is genetically heterogeneous with many mutations reported in each of the complementation group (Strathdee et al., 1992; Joenje et al., 1997, 2000). So far, eight complementation groups: A, B, C, D1, D2, E, F and G (Strathdee et al., 1992; Lo Ten Foe et al., 1996; de Winter et al., 1998; de Winter et al., 2000; Timmers et al., 2001) have been identified. The present example relates to correction of defects in the human FA complementation group C (FANCC) gene. However, the methods of the present invention can equally be used to correct genetic defects in any human gene associated with Fanconi Anemia, or with any other disease or condition caused by known defects in the nucleotide sequence of specific genes.

Isolation of MAPC from FA Patients

Human MAPCs are isolated and cultured as described in Example 2.

Correction of the Human FANCC Gene by Homolgous Recombination

Correction vectors are made by cloning a region from the "wild type" human FANCC gene that spans the region that is disrupted/mutated in the patient, into a suitable commercially available cloning and/or expression vector, as described in Example 7. Locations and sequences of known mutations in the human FANCC gene, can readily be obtained from genome databases known in the art, such as the Human Gene Mutation Database (HGMD®). Correction vectors are made to contain homolgous sequence from the wild type FANCC gene, both upstream and downstream of the disruption or mutation to be corrected. The homolgous regions are sufficiently long to allow homolgous recombination of the correction vector and the patients' FANCC gene to occur. Correction vectors having homologous regions from 3-5 kb in length can be made and used. FIGS. 8 and 9 show the sequences of the wild type human FANCC cDNA and protein, respectively. The genomic sequence of the wild type human FANCC gene can be readily obtained from human genome sequence databases known to those of skill in the art.

Human MAPCs derived from the patient are transfected as described in Example 7 with a correction vector. After transfection, the non-defective nucleotide sequence contained in the correction vector homologously recombines with the defective gene in a proportion of the patient's MAPCs, thereby correcting the genetic defect in those cells. Corrected cells are selected by exposing the MAPCs to doses of cyclophosphamide and/or irradiation that are toxic to the defective cells FANCC cells but not toxic to cells expressing the corrected gene (Noll et al., 2001).

Characterization of the Corrected Cells.

The correction of the FANCC gene in the human MAPCs is confirmed using RT-PCR and/or sequence analysis. The predominant cellular phenotype of FA is chromosomal instability and hypersensitivity to DNA cross linking agents such as mitomycin C and cyclophosphamide (Sasaki & Tonomura, 1973; Auerbach & Wolman, 1976; Ishida & Buchwald, 1982). Therefore, a reduction in sensitivity to mitomycin C and/or cyclophosphamide, and a reduction in chromosomal instability, are also used as measure of phenotypic correction of the human MAPCs.

(a) RT PCR Analysis.

Total cytoplamsic RNA is isolated from patient's non-corrected MAPCs, corrected MAPCs and wild type "reference" MAPCs derived from individuals not affected with FA. Reverse transcription with random hexamer primers is performed to generate a cDNA copy of the mRNA, using standard procedures known in the art. This cDNA is then used as the template in PCR reactions. Primer sequences based on the human FANCC sequence are chosen according to standard procedures. The forward primer used has sequence from a region of the gene upstream of the genetic defect, and the reverse primer has sequence from a region downstream of the genetic defect. PCR products are radioactively labeled by incorporation of $^{32}P$ dATP into the PCR reaction mixture. PCR products are separated on a polyacrylamide gel and the gel is exposed to a phosphorimager screen overnight. Confirmation of the correction of the patient's FANCC gene is obtained by comparison of the PCR product bands in the presumed corrected and the reference wild type human MAPCs. The major PCR product in MAPCs that have been corrected is the same size as that found in wild-type MAPCs, but differs in size from that found in uncorrected MAPCs originally derived from the patient.

(b) Sequence Analysis

Where the genetic defect being corrected is small (for example a point mutation), and therefore can not be distinguished from the wild type version of the gene by differences in the size of PCR products, sequence analysis is performed to check that the patient's corrected cells contain the wild type, as opposed to the defective, sequence. Such sequence analysis is performed by standard techniques known in the art.

(c) Cell Cycle Analysis

FA cells are known to arrest at the G2 phase of the cell cycle following treatment with mitomycin C (Heinrich et al., 1998), therefore functional correction of the patient's FANCC gene defect can be tested by determining if mitomycin C causes G2 arrest in the corrected cells. This is performed as described in example 7.

(d) Chromosome Breakage Analysis.

FA cells are known to exhibit increased chromosomal breakage and radial formation (Auerbach & Wolman, 1976; Auerbach, 1993). Therefore, functional correction of the patient's MAPCs is tested by comparing chromosome breakage of the corrected cells, to that in the patient's original defective cells, and wild type "reference cells". This is performed as described in example 7.

Transplantation of Corrected Cells

Approximately $1 \times 10^6$ corrected cells are transplanted into the patient intravenously. The exact number of cells and dosage frequency of administration will be determined by the skilled artisan based on the patient's weight, age, sex and severity of the defect.

REFERENCES

Alison, M., & Sarraf, C. (1998). Hepatic stem cells. *J Hepatol* 29: 678-83.
Anderson, D. C. et al. (1993). Tumor retention of antibody Fab fragments is enhanced by an attached HIV TAT protein-derived peptide. *Biochem. Biophys Res Commun.* 194:876-884
Araki, K. et al., (1995). Site-specific recombination of a transgene in fertilized eggs by transient expression of a Cre recombinase. *Proc. Natl. Acad. Sci. U.S.A* 92:160-164
Auerbach, A. D. & Wolman, S. R. (1976). *Nature* 261:494-496
Auerbach, A. D. (1993). *Exp. Hematol.* 21:731-733
Bandyopadhyay, et al., (1999). Nucleotide exchange in genomic DNA of rat hepatocytes using RNA/DNA oligonucleotides. Targeted delivery of liposomes and polyethyleneimine to the asialoglycoprotein receptor. *J Biol Chem.* 274:10163-72.
Caplan, A., et al., U.S. Pat. No. 5,486,359
Caplan, A., et al., U.S. Pat. No. 5,811,094
Caplan, A., et al., U.S. Pat. No. 5,837,539
Carreau, A. et al., (1998). *Blood* 91:2737-2744
Carter, P. J. & Samulski, R. J. (2000). Adeno-associated viral vectors as gene delivery vehicles. *Int. J. Mol. Med.* 6:17-27.
Casey, B. P. & Glazer, P. M. (2001). Gene targeting via triple-helix formation. *Prog. Nucleic Acid Res. Mol. Biol.* 67 163-92.
Cassiede P. et al., (1996). Osteochondrogenic potential of marrow mesenchymal progenitor cells exposed to TGF-beta 1 or PDGF-BB as assayed in vivo and in vitro. *J Bone Miner Res.* 9:1264-73.
Choi, K. (1998). Hemangioblast development and regulation. *Biochem Cell Biol.* 76:947-956.
Choi, K. et al., (1998). A common precursor for hematopoietic and endothelial cells. *Development.* 125:725-732.
Clarke, D. L. et al., (2000). Generalized potential of adult NSCs. *Science* 288:1660-3.
De Winter, J. P. et al., (1998). *Nature Genetics* 20:281-283
De Winter, J. P. et al., (2000). *Hum. Mol. Genet.* 9:2665-22674
De Winter, J. P. et al., (2000). *Nature Genetics* 24:15-16
DiGuisto, et al., U.S. Pat. No. 5,681,599
Fanconi (1927). *Janrb. Kinderh.* 117: 257-280
Fawell, S. et al. (1994). Tat-mediated delivery of heterologous proteins into cells. *Proc. Natl. Acad. Sci. USA.* 91:664-668
Fei, R., et al., U.S. Pat. No. 5,635,387
Fridenshtein, A. (1982). Stromal bone marrow cells and the hematopoietic microenvironment. *Arkh Patol* 44:3-11.
Furcht et al. International Application No. PCT/US00/21387.
Gage, F. H. (2000). Mammalian NSCs. *Science* 287:1433-1438.
Goncz, K. K. et al., (2001). Expression of DeltaF508 CFTR in normal mouse lung after site-specific modification of CFTR sequences by SFHR. *Gene Ther.* 8:961-5.
Gronthos, S. et al., (1994). The STRO-1+ fraction of adult human bone marrow contains the osteogenic precursors. *Blood* 84: 4164-73.
Hatada et al. (2001). *Proc. Natl. Acad. Sci.* 97:13807-13811.
Heinrich, M. C. et al., (1998). *Blood* 91; 275-287
Hill, B. et al. (1996). High-level expression of a novel epitope of CD59 identifies a subset of CD34+ bone marrow cells highly enriched for pluripotent stem cells. *Exp Hematol.* 8:936-43.
Hirata, R. K. & Russell, D. W. (2000). Design and packaging of adeno-associated virus gene targeting vectors. *J. Virol.* 74:4612-20.
Hirata, R. et al., (2002). Targeted transgene insertion into human chromosomes by adeno-associated virus vectors. *Nat. Biotechnol.* 20, 735-8.
Inoue, N. et al., (1999). High-fidelity correction of mutations at multiple chromosomal positions by adeno-associated virus vectors. *J. Virol.* 73:7376-80.
Ishida, R. & Buchwald, M. (1982). *Cancer Research* 42:4000-4006
Jaiswal, N., et al., (1997). *J Cell Biochem.* 64(2):295-312.
Jarukamjorn, K et al. (1999). Different regulation of the expression of mouse hepatic cytochrome P450 2B enzymes by glucocorticoid and phenobarbital. *Arch Biochem Biophys* 369:89-99.
Jiang, Y. et al., (2002). Pluripotency of mesenchymal stem cells derived from adult marrow. *Nature* 418:41-49.
Jiang, Y. et al., (2002). Multipotent progenitor cells can be isolated from postnatal murine bone marrow, muscle and brain. *Exp. Hematol.* 8:896-904.
Joenje, H. et al., (1997). *Am. J Hum. Genet.* 61:940-944.
Johnstone, B., Hering, T. M., Caplan, A. I., Goldgberg, V. M., Yoo, J. U. (1998). In vitro chondrogenesis of bone marrow-derived mesenchymal progenitor cells. *Exp Cell Res.* 1:265-72.
Lo Ten Foe, J. R. et al., (1996). *Nature Genet.* 14:320-323
Mann, D. A. & Frankel, A. D. (1991). Endocytosis and targeting of exogenous HIV-1 Tat protein. *EMBO J.* 10:1733-9
Martin, G. R. (1981). Isolation of a pluripotent cell line from early mouse embryos cultured in medium conditioned by teratocaracinoma stem cells. *Proc Natl Acad Sci U.S.A.* 12:7634-8.
Masinovsky, B., U.S. Pat. No. 5,837,670
McGlave, et al., U.S. Pat. No. 5,460,964
Noll, M. et al. (2001). *Mol. Ther.* 3:14023.
Okabe, S., Forsberg-Nilsson, K., Spiro, A. C., Segal, M., and McKay,-R. D. (1996). Development of neuronal precursor cells and functional postmitotic neurons from ES cells in vitro. *Mech Dev* 59:89-102.
Orkin, S. (1998). Embryonic stem cells and transgenic mice in the study of hematopoiesis. *Int. J. Dev. Biol.* 42:927-34.
Palmer, T. D., Takahashi, J., and Gage, F. H. (1997). The adult rat hippocampus contains primordial NSCs. *Mol Cell Neurosci* 8:389-404.
Peault, B. 1996. Hematopoiedc stem cell emergence in embryonic life: developmental hematology revisited. *J. Hematother.* 5:369.
Pittenger, M. F., Mackay, A. M., Beck, S. C., Jaiswal, R. K., Douglas, R., Mosca, J. D., Moorman, M. A., Simonetti, D. W., Craig, S., and Marshak, D. R. (1999). Multilineage potential of adult human MSCs. *Science* 284:143-147.
Pittenger, M., U.S. Pat. No. 5,827,740
Potten, C. (1998). Stem cells in gastrointestinal epithelium: numbers, characteristics and death. *Philos Trans R Soc Lond B Biol Sci* 353:821-30.
Reubinoff, B. E., Pera, M. F., Fong, C. Y., Trounson, A., and Bongso, A. (2000). ES cell lines from human blastocysts: somatic differentiation in vitro. *Nat Biotech* 18:399-404.
Reyes, M., and Verfaillie, C. M. (2001). Characterization of multipotent adult progenitor cells, a subpopulation of mesenchymal stem cells. *Ann N Y Acad Sci* 938:231-233; discussion 233-235.

Reyes, M., Lund, T., Lenvik, T., Aguiar, D., Koodie, L., and Verfaillie, C. M. (2001). Purification and ex vivo expansion of postnatal human marrow mesodermal progenitor cells. *Blood* 98:2615-2625.

Sauer, B. & Henderson, N. (1988). Site-specific DNA recombination in mammalian cells by the Cre recombinase of bacteriophage P1. *Proc. Natl. Acad. Sci. U.S.A* 85:5166-5170

Sasaki, M. S. & Tonomura, A. (1973). *Cancer Research* 33:1829-1836.

Schwartz, et al., U.S. Pat. No. 759,793

Shamblott, M., Axelman, J., Wang, S., Bugg, E., Littlefield, J., Donovan, P., Blumenthal, P., Huggins, G., Gearhart, J.: (1998) Derivation of pluripotent stem cells from cultured human primordial germ cells. *Proc. Natl. Acad. Sci. U.S.A.* 95:13726-31.

Simmons, P., et al., U.S. Pat. No. 5,677,136

Strathdee, C. A. et al., (1992). Evidence for at least four Fanconi anemia genes including FACC on chromosome 9. *Nature Genet.* 1:196-198

Svendsen, C. N., and Caldwell, M. A. (2000). NSCs in the developing central nervous system: implications for cell therapy through transplantation. *Prog Brain Res.* 127:13-34.

Svendsen, C. N., Caldwell, M. A., Ostenfeld, T. (1999). Human neural stem cells: Isolation, expansion and transplantation. *Brain Path* 9:499-513.

Timmers, C. et al., (2001). *Mol. Cell.* 7:241-248

Thomson, J. A., Itskovitz-Eldor, J., Shapiro, S. S., Waknitz, M. A., Swiergiel, J. J., Marshall, V. S., and Jones, J. M. (1998). ES cell lines derived from human blastocysts. *Science* 282:114-7.

Thomson, J., Kalisman J., Golos, J., Durning, M., Harris, C., Becker, R., Hearn, J. (1995) Isolation of a primate embryonic stem cell line. *Proc. Natl. Acad. Sci. U.S.A.* 92:7844-8, Tsukamoto, et al., U.S. Pat. No. 5,750,397

Tsukamoto, et al., U.S. Pat. No. 5,716,827

Tzanakakis, E. S., Hansen, L. K., and Hu, W. S. (2001). The role of actin filaments and microtubules in hepatocyte spheroid self-assembly. *Cell Motil Cytoskeleton* 48:175-189.

Watt, F. (1997). Epidermal stem cells: markers patterning and the control of stem cell fate. *Philos Trans R Soc Lond B Biol Sci* 353: 831-6.

Watt, S., Gschmeissner, S., and Bates, P. (1995). PECAM-1: its expression and function as a cell adhesion molecule on hemopoietic and endothelial cells. *Leuk Lymph.* 17:229.

Williams, R. L., Hilton, D. J., Pease, S., Willson, T. A., Stewart, C. If, Gearing, D. P., Wagner, E. F., Metcalf, D., Nicola, N. A., and Gough, N. M. (1988). Myeloid leukemia inhibitory factor maintains the developmental potential of ES cells. *Nature* 336:684-7.

Whitney, M. et al., (1996). A common mutation in the FACC gene causes Fanconi anaemia in Ashkenazi Jews. *Blood* 88:49-58.

Yanez & Porter. (1999). *Gene Therapy* 6:1282-1290.

Yoo, J. U., Barthel, T. S., Nishimura, K., Solchaga, L., Caplan, A. I., Goldberg, V. M., Johnstone, B. (1998). Then chondrogenic potential of human bone-marrow-derived mesenchymal progenitor cells. *J Bone Joint Surg Am.* 12:1745-57.

Young, H., et al., U.S. Pat. No. 5,827,735

Zambrowicz, B. P., Imamoto, A., Hering, S., Herzenberg, L. A., Kerr, W. G., and Soriano, P. (1997). Disruption of overlapping transcripts in the ROSA beta geo 26 gene trap strain leads to widespread expression of beta-galactosidase in mouse embryos and hematopoietic cells. *Proc Natl Acad Sci USA.* 94:3789-94.

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

We claim:

1. A method of altering gene expression in a cell, the method comprising:
   a) introducing, by nucleoporation, a polynucleotide into isolated expanded human non-embryonic, non-germ cells, with a transfection efficiency up to 14% and without toxicity to the cells, the cells having undergone at least 10-40 cell doublings in culture, wherein the cells are multipotent adult progenitor cells characterized in that they are non-embryonic, non-germ cells that express oct4, are not transformed, and have a normal karyotype, the polynucleotide comprising a sequence of interest; and
   b) culturing the nucleoporated cells produced in step a) under conditions sufficient to express the sequence of interest, such that the resulting cells have altered gene expression.

2. The method of claim 1 wherein the polynucleotide also comprises a sequence homologous to a genomic DNA sequence in the cells and the polynucleotide is homologously recombined in the cells.

3. The method of claim 1 or 2 wherein the non-embryonic, non-germ cells further express one or more of telomerase, rex-1, rox-1, or sox-2.

4. The method of claim 1 or 2 wherein the non-embryonic, non-germ cells can differentiate into at least one cell type of at least two of the endodermal, ectodermal, and mesodermal embryonic lineages.

5. The method of claim 4 wherein the non-embryonic, non-germ cells further express one or more of telomerase, rex-1, rox-1, or sox-2.

6. The method of claim 4 wherein the non-embryonic, non-germ cells can differentiate into at least one cell type of each of the endodermal, ectodermal, and mesodermal embryonic lineages.

7. The method of claim 6 wherein the non-embryonic, non-germ cells further express one or more of telomerase, rex-1, rox-1, or sox-2.

8. The method of claim 1 or 2, further comprising combining the non-embryonic, non-germ cells produced in step b) with a pharmaceutically-acceptable carrier.

9. The method of claim 1 or 2, wherein the non-embryonic, non-germ cells are cultured at a density of about 500 cells/cm$^2$-1500 cells/cm$^2$.

10. The method of claim 9, wherein the non-embryonic, non-germ cells are cultured at a density of about 500 cells/cm$^2$.

11. The method of claim 1, wherein the non-embryonic, non-germ cells are isolated from bone marrow.

* * * * *

SEQUENCE LISTING

```
<160> NUMBER OF SEQ ID NOS: 5

<210> SEQ ID NO 1
<211> LENGTH: 1674
<212> TYPE: DNA
<213> ORGANISM: Homo sapiens

<400> SEQUENCE: 1
atggctcaag attcagtaga tctttcttgt gattatcagt tttggatgca gaagctttct      60
gtatgggatc aggcttccac tttggaaacc cagcaagaca cctgtcttca cgtggctcag     120
ttccaggagt tcctaaggaa gatgtatgaa gccttgaaag agatggattc taatacagtc     180
attgaaagat tccccacaat tggtcaactg ttggcaaaag cttgttggaa tccttttatt     240
ttagcatatg atgaaagcca aaaaattcta atatggtgct tatgttgtct aattaacaaa     300
gaaccacaga attctggaca atcaaaactt aactcctgga tacagggtgt attatctcat     360
atactttcag cactcagatt tgataaagaa gttgctcttt tcactcaagg tcttgggtat     420
gcacctatag attactatcc tggtttgctt aaaaatatgg ttttatcatt agcgtctgaa     480
ctcagagaga atcatcttaa tggatttaac actcaaaggc gaatggctcc cgagcgagtg     540
gcgtccctgt cacgagtttg tgtcccactt attaccctga cagatgttga cccctggtg     600
```

```
gaggctctcc tcatctgtca tggacgtgaa cctcaggaaa tcctccagcc agagttcttt      660
gaggctgtaa acgaggccat tttgctgaag aagatttctc tccccatgtc agctgtagtc      720
tgcctctggc ttcggcacct tcccagcctt gaaaaagcaa tgctgcatct tttttgaaaag    780 ctaatctcca gtgagagaaa ttgtctgaga aggatcgaat gctttataaa agattcatcg      840
ctgcctcaag cagcctgcca ccctgccata ttccgggttg ttgatgagat gttcaggtgt      900
gcactcctgg aaaccgatgg ggccctggaa atcatagcca ctattcaggt gtttacgcag      960
tgctttgtag aagctctgga gaaagcaagc aagcagctgc ggtttgcact caagacctac     1020
tttccttaca cttctccatc tcttgccatg gtgctgctgc aagaccctca agatatccct     1080
cggggacact ggctccagac actgaagcat atttctgaac tgctcagaga agcagttgaa     1140
gaccagactc atgggtcctg cggaggtccc tttgagagct ggttcctgtt cattcacttc     1200
ggaggatggg ctgagatggt ggcagagcaa ttactgatgt cggcagccga accccccacg     1260
gccctgctgt ggctcttggc cttctactac ggccccgtg atgggaggca gagagcacag      1320
actatggtcc aggtgaaggc cgtgctgggc cacctcctgg caatgtccag aagcagcagc     1380
ctctcagccc aggacctgca gacggtagca ggacagggca cagacacaga cctcagagct     1440
cctgcacaac agctgatcag gcaccttctc ctcaacttcc tgctctgggc tcctggaggc     1500
cacacgatcg cctgggatgt catcaccctg atggctcaca ctgctgagat aactcacgag     1560
atcattggct ttcttgacca gaccttgtac agatggaatc gtcttggcat tgaaagccct     1620
agatcagaaa aactggcccg agagctcctt aaagagctgc gaactcaagt ctag           1674
```

<210> SEQ ID NO 2
<211> LENGTH: 557
<212> TYPE: PRT
<213> ORGANISM: Homo sapiens

<400> SEQUENCE: 2

```
Met Ala Gln Asp Ser Val Asp Leu Ser Cys Asp Tyr Gln Phe Trp Met
 1               5                  10                  15

Gln Lys Leu Ser Val Trp Asp Gln Ala Ser Thr Leu Glu Thr Gln Gln
            20                  25                  30

Asp Thr Cys Leu His Val Ala Gln Phe Gln Glu Phe Leu Arg Lys Met
        35                  40                  45

Tyr Glu Ala Leu Lys Glu Met Asp Ser Asn Thr Val Ile Glu Arg Phe
    50                  55                  60

Pro Thr Ile Gly Gln Leu Leu Ala Lys Ala Cys Trp Asn Pro Phe Ile
65                  70                  75                  80

Leu Ala Tyr Asp Glu Ser Gln Lys Ile Leu Ile Trp Cys Leu Cys Cys
                85                  90                  95

Leu Ile Asn Lys Glu Pro Gln Asn Ser Gly Gln Ser Lys Leu Asn Ser
           100                 105                 110

Trp Ile Gln Gly Val Leu Ser His Ile Leu Ser Ala Leu Arg Phe Asp
       115                 120                 125

Lys Glu Val Ala Leu Phe Thr Gln Gly Leu Gly Tyr Ala Pro Ile Asp
   130                 135                 140

Tyr Tyr Pro Gly Leu Leu Lys Asn Met Val Leu Ser Leu Ala Ser Glu
145                 150                 155                 160

Leu Arg Glu Asn His Leu Asn Gly Phe Asn Thr Gln Arg Arg Met Ala
                165                 170                 175

Pro Glu Arg Val Ala Ser Leu Ser Arg Val Cys Val Pro Leu Ile Thr
```

```
                    180                 185                 190
Leu Thr Asp Val Asp Pro Leu Val Glu Ala Leu Leu Ile Cys His Gly
            195                 200                 205

Arg Glu Pro Gln Glu Ile Leu Gln Pro Glu Phe Phe Glu Ala Val Asn
        210                 215                 220

Glu Ala Ile Leu Leu Lys Lys Ile Ser Leu Pro Met Ser Ala Val Val
225                 230                 235                 240

Cys Leu Trp Leu Arg His Leu Pro Ser Leu Glu Lys Ala Met Leu His
                245                 250                 255

Leu Phe Glu Lys Leu Ile Ser Ser Glu Arg Asn Cys Leu Arg Arg Ile
            260                 265                 270

Glu Cys Phe Ile Lys Asp Ser Ser Leu Pro Gln Ala Ala Cys His Pro
        275                 280                 285

Ala Ile Phe Arg Val Val Asp Glu Met Phe Arg Cys Ala Leu Leu Glu
        290                 295                 300

Thr Asp Gly Ala Leu Glu Ile Ile Ala Thr Ile Gln Val Phe Thr Gln
305                 310                 315                 320

Cys Phe Val Glu Ala Leu Glu Lys Ala Ser Lys Gln Leu Arg Phe Ala
                325                 330                 335

Leu Lys Thr Tyr Phe Pro Tyr Thr Ser Pro Ser Leu Ala Met Val Leu
            340                 345                 350

Leu Gln Asp Pro Gln Asp Ile Pro Arg Gly His Trp Leu Gln Thr Leu
        355                 360                 365

Lys His Ile Ser Glu Leu Leu Arg Glu Ala Val Glu Asp Gln Thr His
        370                 375                 380

Gly Ser Cys Gly Gly Pro Phe Glu Ser Trp Phe Leu Phe Ile His Phe
385                 390                 395                 400

Gly Gly Trp Ala Glu Met Val Ala Glu Gln Leu Leu Met Ser Ala Ala
                405                 410                 415

Glu Pro Pro Thr Ala Leu Leu Trp Leu Leu Ala Phe Tyr Tyr Gly Pro
            420                 425                 430

Arg Asp Gly Arg Gln Arg Ala Gln Thr Met Val Gln Val Lys Ala Val
        435                 440                 445

Leu Gly His Leu Leu Ala Met Ser Arg Ser Ser Ser Leu Ser Ala Gln
        450                 455                 460

Asp Leu Gln Thr Val Ala Gly Gln Gly Thr Asp Thr Asp Leu Arg Ala
465                 470                 475                 480

Pro Ala Gln Gln Leu Ile Arg His Leu Leu Asn Phe Leu Leu Trp
                485                 490                 495

Ala Pro Gly Gly His Thr Ile Ala Trp Asp Val Ile Thr Leu Met Ala
            500                 505                 510

His Thr Ala Glu Ile Thr His Glu Ile Ile Gly Phe Leu Asp Gln Thr
        515                 520                 525

Leu Tyr Arg Trp Asn Arg Leu Gly Ile Glu Ser Pro Arg Ser Glu Lys
        530                 535                 540

Leu Ala Arg Glu Leu Leu Lys Glu Leu Arg Thr Gln Val
545                 550                 555

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 3
ctgccaacct gccatcttca g                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aagagcagct agtacttctg g                                              21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aggaaagtag gtcctgaggg                                                20
```